US008674132B2

(12) United States Patent
Toscano et al.

(10) Patent No.: US 8,674,132 B2
(45) Date of Patent: Mar. 18, 2014

(54) N-HYDROXYLSULFONAMIDE DERIVATIVES AS NEW PHYSIOLOGICALLY USEFUL NITROXYL DONORS

(75) Inventors: John P. Toscano, Glen Arm, MD (US); Frederick Arthur Brookfield, Abingdon (GB); Andrew D. Cohen, New York, NY (US); Stephen Martin Courtney, Abingdon (GB); Lisa Marie Frost, Abingdon (GB); Vincent Jacob Kalish, Annapolis, MD (US)

(73) Assignees: The Johns Hopkins University, Baltimore, MD (US); Cardioxyl Pharmaceuticals, Inc., Chapel Hill, NC (US)

(*) Notice: Subject to any disclaimer, the term of this patent is extended or adjusted under 35 U.S.C. 154(b) by 0 days.

(21) Appl. No.: 13/531,364

(22) Filed: Jun. 22, 2012

(65) Prior Publication Data

US 2012/0258965 A1   Oct. 11, 2012

Related U.S. Application Data

(63) Continuation of application No. 12/239,705, filed on Sep. 26, 2008, now Pat. No. 8,227,639.

(60) Provisional application No. 60/995,636, filed on Sep. 26, 2007.

(51) Int. Cl.
*C07C 303/00* (2006.01)

(52) U.S. Cl.
USPC ............................................. 564/90; 514/604

(58) Field of Classification Search
None
See application file for complete search history.

(56) References Cited

U.S. PATENT DOCUMENTS

| | | | |
|---|---|---|---|
| 3,751,255 A | 8/1973 | Wilson et al. | |
| 4,369,174 A | 1/1983 | Nagal et al. | |
| 4,663,351 A | 5/1987 | Diamond | |
| 4,798,824 A | 1/1989 | Belzer et al. | |
| 4,842,866 A | 6/1989 | Horder et al. | |
| 5,217,720 A | 6/1993 | Sekigawa et al. | |
| 6,525,081 B1 | 2/2003 | Matsumoto et al. | |
| 6,569,457 B2 | 5/2003 | Ullah et al. | |
| 6,638,534 B1 | 10/2003 | Ishibashi et al. | |
| 6,936,639 B2 | 8/2005 | Wink et al. | |
| 8,030,356 B2 * | 10/2011 | Toscano et al. | 514/604 |
| 8,227,639 B2 * | 7/2012 | Toscano et al. | 564/90 |
| 2004/0038947 A1 | 2/2004 | Wink et al. | |
| 2005/0153966 A1 | 7/2005 | Gangloff et al. | |
| 2005/0192254 A1 | 9/2005 | Wink et al. | |
| 2007/0299107 A1 | 12/2007 | Toscano et al. | |

FOREIGN PATENT DOCUMENTS

| | | |
|---|---|---|
| JP | 4-321671 | 11/1992 |
| SU | 186456 | 10/1966 |
| WO | WO 01/10827 A1 | 2/2001 |
| WO | WO 02/100810 | 12/2002 |
| WO | WO 2005/074598 A2 | 8/2005 |
| WO | WO 2005/074598 A3 | 8/2005 |
| WO | WO 2006/086188 A2 | 8/2006 |
| WO | WO 2006/086188 A3 | 8/2006 |
| WO | WO 2007/002444 A1 | 1/2007 |
| WO | WO 2007/109175 A1 | 9/2007 |
| WO | WO 2009/042970 A1 | 4/2009 |

OTHER PUBLICATIONS

Andrewes et al., "Experimental Chemotherapy of Typhus: Anti-Rickettsial Action of p-Sulphonamidobenzamidine and Related Compounds," *Proc. R. Soc. Lond., B, Biol. Sci.* 133(1):20-62 (1946).
Backx, "The Relationship Between Contractile Force and Intracellular [$Ca^{2+}$] in Intact Rat Cardiac Trabeculae," *J. Gen. Physiol.* 105:1-19 (1995).
Baerlocher et al., "Few and More Potent Antifungal Disulfides," *Aust. J. Chem.* 53(1):1-5 (2000).
Baumgarth et al., "(2-Methyl-5-(methylsulfonyl)benzoyl)guanidine $Na^+/H^+$ Antiporter Inhibitors," *J. Med. Chem.* 40(13):2017-2034 (1997).
Bonner et al., "Kinetic, Isotropic, and $^{15}N$ NMR Study of N-Hydroxybenzenesulfonamide Decomposition: An HNO Source Reaction," *Inorg. Chem.* 31(10-13):2514-2519 (1992).
Bouzamondo et al., "Beta-Blocker Treatment in Heart Failure," *Fundam. Clin. Pharmacol.* 15(2):95-109 (2001).
Bristow et al., "Inotropes and β-Blockers: Is There a Need for New Guidelines?" *J. Card. Fail.* 7(2 Suppl. 1): 8-12 (2001).
Brynes et al., "Potential Antitumor Agents via Inhibitors of L-Asparagine Synthetase: Substituted Sulfonamides and Sulfonyl Hydrazides Related to Glutamine," *J. Pharm. Sci.*, 67(11):1550-1553 (1978).
Brynes et al., "Potential Inhibitors of L-Asparagine Biosynthesis. 4. Substituted Sulphonamide and Sulfonylhydrazide Analogues of L-Asparagine," *J. Med. Chem.*, 21(1):45-49 (1978).
Caplus. Accession No. 2002:176265, Japanese Patent Publication No. 2002-072459-A, one page (2002).
Chemcats. Accession No. 2033522701, *Enamine Building Blocks*, Enamine: Kiev, UK, one page (2008).
Chemcats. Accession No. 2033715491, *Enamine Screening Library*, Enamine: Kiev, UK, one page (2008).
Chemcats. Accession No. 2037996565, *Aurora Screening Library*, Aurora Fine Chemicals, LLC: San Diego, CA, one page (2008).
Crawford et al., "Hypoxia, Red Blood Cells, and Nitrite Regulate NO-Dependent Hypoxic Vasodilation," *Blood* 107(2):566-574 (2006, e-pub 2005).

(Continued)

*Primary Examiner* — Sudhakar Katakam
(74) *Attorney, Agent, or Firm* — Dechert LLP

(57) ABSTRACT

The invention relates to N-hydroxylsulfonamide derivatives that donate nitroxyl (HNO) under physiological conditions and are useful in treating and/or preventing the onset and/or development of diseases or conditions that are responsive to nitroxyl therapy, including heart failure and ischemia/reperfusion injury. Novel N-hydroxylsulfonamide derivatives release NHO at a controlled rate under physiological conditions, and the rate of HNO release is modulated by varying the nature and location of functional groups on the N-hydroxylsulfonamide derivatives.

22 Claims, 1 Drawing Sheet

(56) References Cited

OTHER PUBLICATIONS

Database CAPlus Abstract Accession No. 1994:645157 (concerning Zani et al., "Antimicrobial and Genotoxic Properties of Quinoline Derivatives," *Bollettino Chimico Farmaceutico*, 133(5):328-338 (May 1994)), Chemical Abstracts Service, Columbus, Ohio (1994).
Fukuto et al., "The Physiological Chemistry and Biological Activity of Nitroxyl (HNO): The Neglected, Misunderstood, and Enigmatic Nitrogen Oxide," *Chem. Res. Toxicol.* 18(5):790-801 (2005).
Gao et al., "Myofilament $Ca^{2+}$ Sensitivity in Intact Versus Skinned Rat Ventricular Muscle," *Circ. Res.* 74:408-415 (1994).
Gao et al., "Relationship Between Intracellular Calcium and Contractile Force in Stunned Myocardium: Direct Evidence for Decreased Myofilament $Ca^{2+}$ Responsiveness and Altered Diastolic Function in Intact Ventricular Muscle," *Circ. Res.* 76(6):1036-1048 (1995).
Gao et al., "Calcium Cycling and Contractile Activation in Intact Mouse Cardiac Muscle," *J. Physiol.* 507(1):175-184 (1998).
Hare et al., "Nitric Oxide Inhibits and Positive Inotropic Response to β-Adrenergic Stimulation in Humans with Left Ventricular Dysfunction," *Circulation* 92(8):2198-2203 (1995).
Hare et al., "Pertussis Toxin-senstive G Proteins Influence Nitric Oxide Synthase III Activity and Protein Levels in Rat Heart," *J. Clin. Invest.* 101(6):1424-1431 (1998).
Hart et al., "Differential Effects of Natriuretic Peptides and NO on LV Function in Heart Failure and Normal Dogs," *Am. J. Physiol. Heart Circ. Physiol.* 281(1):H146-H154 (2001).
Ingall, "Preventing Ischemic Stroke: Current Approaches to Primary and Secondary Prevention," *Postgrad. Med.* 107(6):34-50 (2000).
International Preliminary Report on Patentability, International Application No. PCT/US2007/006710 (published as WO 2007/109175) (mailed Sep. 23, 2008).
International Search Report, International Application No. PCT/US2007/006710 (published as WO 2007/109175) (mailed Aug. 22, 2007).
International Search Report, International Application No. PCT/US2008/078024 filed Sep. 26, 2008, eight pages, (mailed Jan. 23, 2009).
Jackman et al., "Studies in the Field of Diuretic Agents. Part VIII. Some Miscellaneous Derivatives," *J. Pharm. Pharmacol.* 15:202-211 (1963).
Katori et al., "Calcitonin Gene-Related Peptide in Vivo Positive Inotropy is Attributable to Regional Sympatho-Stimulation and is Blunted in Congestive Heart Failure," *Circ. Res.* 96(2):234-243 (2005, e-pub 2004).
Lowes et al., "Inotropes in the Beta-Blocker Era," *Clin. Cardiol.* 23(Suppl. III):III-II-III-16 (2000).
Ma et al. "Opposite Effects of Nitric Oxide and Nitroxyl on Postischemic Myocardial Injury," *Proc. Natl. Acad. Sci. USA* 96(25):14617-14622 (1999).
Mincione et al., "Carbonic Anhydrase Inhibitors: Inhibition of Isozymes I, II and IV with N-Hydroxysulfonamides—A Novel Class of Intraocular Pressure Lowering Agents," *J. Enzyme Inhibition* 13(4):267-284 (1998).
Nagasawa et al., "Prodrugs of Nitroxyl as Potential Aldehyde Dehydrogenase Inhibitors Vis-à-vis Vascular Smooth Muscle Relaxants," *J. Med. Chem.* 38(11):1865-1871 (1995).
Paolocci et al., "cGMP-Independent Inotropic Effects of Nitric Oxide and Peroxynitrite Donors: Potential Role for Nitrosylation," *Am. J. Physiol. Heart Circ. Physiol.* 279(4):H1982-H1988 (2000).
Rastaldo et al., "Cytochrome P-450 Metabolite of Arachidonic Acid Mediates Bradykinin-Induced Negative Intotropic Effect," *Am. J. Physiol. Heart Circ. Physiol.* 280(6):H2823-2832 (2001).
Registry. Accession No. 790725-76-7, one page (2004).
Registry. Accession No. 920663-30-5, one page (2007).
Registry. Accession No. 930060-34-7, one page (2007).
Scozzafava et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit Both Theses Zinc Enzymes," *J. Med. Chem.* 43(20):3677-3687 (2000).
Scozzafava et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit Both These Zinc Enzymes," Erratum, *J. Med. Chem.* 44(6):1016 (2001).
Singapore Search Report and Written Opinion, Singapore Application No. 200806554-2 (Jan. 4, 2010) (17pages).
Slotwiner-Nie et al., "Infectious Diarrhea in the Elderly," *Gastroenterol. Clin. N. Am.* 30(3):625-635 (2001).
Suzuki et al., "Novel Inhibitors of Human Histone Deacetylases: Design, Synthesis, Enzyme Inhibition and Cancer Cell Growth Inhibition of SAHA-Based Nonhydroxamates," *J. Med. Chem.*, 48(4):1019-1032 (2005).
Takahira et al., "Dexamethasone Attenuates Neutrophil Infiltration in the Rat Kidney in Ischemia-Reperfusion Injury: The Possible Role of Nitroxyl," *Free Radic. Biol. Med.* 31(6):809-815 (2001).
Thevis et al., "High Speed Determination of Beta-Receptor Blocking Agents in Human Urine by Liquid Chromatography/Tandem Mass Spectrometry," *Biomed. Chromatogr.* 15(6):393-402 (2001).
U.S. Appl. No. 11/815,203, filed Jan. 31, 2005 (International filing date), Ray et al.
U.S. Appl. No. 11/922,793, filed Jun. 23, 2006 (International filing date), Paolocci et al.
Written Opinion mailed on Jan. 23, 2009, for PCT Application No. PCT/US2008/078024, filed Sep. 26, 2008, six pages.
Wrobel et al., "Synthesis of (bis)Sulfonic Acid, (bis)Benzamides as Follicle-Stimulating Hormone (FSH) Antagonists," *Biorg. Med. Chem.* 10(3):639-656 (2002).
Zamora et al., "Oxidative Release of Nitric Oxide Accounts for Guanylyl Cyclase Stimulating, Vasodilator and Anti-Platelet Activity of Piloty's Acid: A Comparison with Angeli's Salt," *Biochem. J.* 312:333-339 (1995).
Zani et al., "Antimicrobial and genotoxic properties of quinoline derivatives," *Bollettino Chimico Farmaceutico*, 133(5):328-338 (1994).
Office Action for corresponding Japanese Patent Application No. 2010-27222 dated Aug. 13, 2013.

* cited by examiner

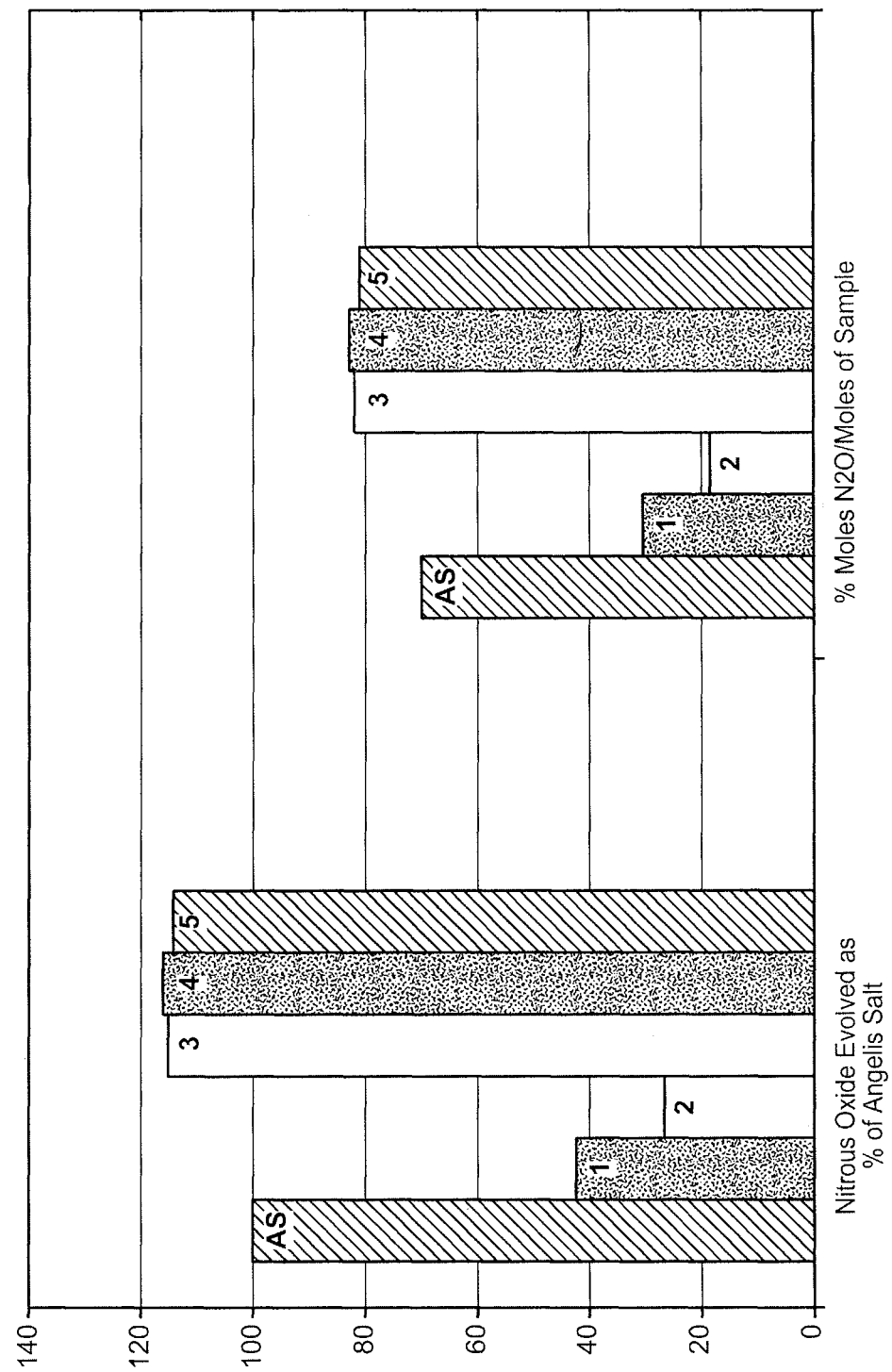

N-HYDROXYLSULFONAMIDE DERIVATIVES AS NEW PHYSIOLOGICALLY USEFUL NITROXYL DONORS

CROSS-REFERENCE TO RELATED APPLICATIONS

This application is a continuation of U.S. patent application Ser. No. 12/239,705, filed Sep. 26, 2008, now U.S. Pat. No. 8,227,639, which claims benefit under 35 U.S.C. §119(e) to U.S. Provisional Patent Application Ser. No. 60/995,636, filed Sep. 26, 2007, the contents of which are incorporated herein by reference.

STATEMENT REGARDING FEDERALLY SPONSORED RESEARCH OR DEVELOPMENT

This invention was made in part with government support under Grant No. CHE-0518406 from the National Science Foundation. The government may have certain rights in this invention.

BACKGROUND OF THE INVENTION

Summary of Heart Failure

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. Often, an individual experiencing heart failure will have some degree of both systolic heart failure and diastolic heart failure.

CHF is also classified according to its severity. The New York Heart Association classifies CHF into four classes: Class I involves no obvious symptoms, with no limitations on physical activity; Class II involves some symptoms during or after normal activity, with mild physical activity limitations; Class III involves symptoms with less than ordinary activity, with moderate to significant physical activity limitations; and Class IV involves significant symptoms at rest, with severe to total physical activity limitations. Typically, an individual progresses through the classes as they live with the condition.

Although CHF is generally thought of as a chronic, progressive condition, it can also develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema and dyspnea.

Common treatment agents for CHF include vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have become standard agents for treating mild to moderate heart failure. Lowes et al, *Clin. Cardiol.*, 23:III11-6 (2000).

Positive inotropic agents include beta-adrenergic agonists, such as dopamine, dobutamine, dopexamine, and isoproterenol. However, use of a beta-agonist has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., *Fundam. Clin. Pharmacol.*, 15: 95-109 (2001). Accordingly, they have become an established therapy for heart failure. However, even subjects that improve under beta-antagonist therapy may subsequently decompensate and require acute treatment with a positive inotropic agent. Unfortunately, as their name suggests, beta-antagonists block the mechanism of action of the positive inotropic beta-agonists that are used in emergency care centers. Bristow et al., *J. Card. Fail.*, 7: 8-12 (2001).

Vasodilators, such as nitroglycerin, have been used for a long period of time to treat heart failure. However, the cause of nitroglycerin's therapeutic effect was not known until late in the last century when it was discovered that the nitric oxide molecule (NO) was responsible for nitroglycerin's beneficial effects. In some subjects experiencing heart failure, a nitric oxide donor is administered in combination with a positive inotropic agent to both cause vasodilation and to increase myocardial contractility. However, this combined administration can impair the effectiveness of positive inotropic treatment agents. For example, Hart et al, *Am. J. Physiol. Heart Circ. Physiol.*, 281:146-54 (2001) reported that administration of the nitric oxide donor sodium nitroprusside, in combination with the positive inotropic, beta-adrenergic agonist dobutamine, impaired the positive inotropic effect of dobutamine. Hare et al., *Circulation*, 92:2198-203 (1995) also disclosed the inhibitory effect of nitric oxide on the effectiveness of dobutamine.

As described in U.S. Pat. No. 6,936,639, compounds that donate nitroxyl (HNO) under physiological conditions have both positive inotropic and lusitropic effects and offer significant advantages over existing treatments for failing hearts. Due to their concomitant positive inotropic/lusotropic action and unloading effects, nitroxyl donors were reported as helpful in treating cardiovascular diseases characterized by high resistive load and poor contractile performance. In particular, nitroxyl-donating compounds were reported as useful in the treatment of heart failure, including heart failure in individuals receiving beta-antagonist therapy.

Summary of Ischemia

Ischemia is a condition characterized by an interruption or inadequate supply of blood to tissue, which causes oxygen deprivation in the affected tissue. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. Further, upon reperfusion with subsequent reoxygenation of the tissue, when the blood is able to flow again or the oxygen demand of the tissue subsides, additional injury can be caused by oxidative stress.

Ischemia/reperfusion injury refers to tissue damage caused by oxygen deprivation followed by reoxygenation. The effects of ischemia/reperfusion injury in a subject experiencing the condition can be fatal, particularly when the injury occurs in a critical organ such as the heart or brain.

Accordingly, compounds and compositions effective in preventing or protecting against ischemia/reperfusion injury would be useful pharmaceuticals. Compounds such as nitroglycerin have been used for a long period of time to help control vascular tone and protect against myocardial ischemia/reperfusion injury. It was discovered that the nitric oxide molecule was responsible for nitroglycerin's beneficial effects. This discovery prompted interest in medical uses for nitric oxide and investigations into related species such as nitroxyl. As reported in U.S. patent application Ser. No. 10/463,084 (U.S. Publication No. 2004/0038947) administration of a compound that donates nitroxyl under physiological conditions, prior to ischemia, can attenuate ischemia/reperfusion injury to tissues, for example, myocardial tissues. This beneficial effect was reported as a surprising result given that nitroxyl was previously reported to increase ischemia/reperfusion injury (See, Ma et al., "Opposite Effects of Nitric Oxide and Nitroxyl on Postischemic Myocardial Injury," *Proc. Nat'l Acad. Sci.*, 96(25): 14617-14622 (1999), reporting that administration of Angeli's salt (a nitroxyl donor under physiological conditions) to anesthetized rabbits during ischemia and 5 minutes prior to reperfusion increased myocardial ischemia/reperfusion injury and Takahira et al., "Dexamethasone Attenuates Neutrophil Infiltration in the Rat Kidney in Ischemia/Reperfusion Injury: The Possible Role of Nitroxyl," *Free Radical Biology & Medicine*, 31(6):809-815 (2001) reporting that administration of Angeli's salt during ischemia and 5 minutes before reperfusion of rat renal tissue contributed to neutrophil infiltration into the tissue, which is believed to mediate ischemia/reperfusion injury). In particular, pre-ischemic administration of Angeli's salt and isopropylamine/NO has been reported to prevent or reduce ischemia/reperfusion injury.

Summary of Nitroxyl Donors

To date, the vast majority of studies of the biological effect of HNO have used the donor sodium dioxotrinitrate ("Angeli's salt" or "AS"). However, the chemical stability of AS has made it unsuitable to develop as a therapeutic agent. N-hydroxybenzenesulfonamide ("Piloty's acid" or "PA") has previously been shown to be a nitroxyl donor at high ph (>9) (Bonner, F. T.; Ko, Y. *Inorg. Chem.* 1992, 31, 2514-2519). However, under physiological conditions, PA is a nitric oxide donor via an oxidative pathway (Zamora, R.; Grzesiok, A.; Weber, H.; Feelisch, M. *Biochem. J.* 1995, 312, 333-339). Thus, the physiological effects of AS and PA are not the same because AS is a nitroxyl donor under physiological conditions whereas PA is a nitric oxide donor under physiological conditions.

Although U.S. Pat. No. 6,936,639 and U.S. Publication No. 2004/0038947 describe PA as a compound that donates nitroxyl and note that other sulfohydroxamic acids and their derivatives are therefore also useful as nitroxyl donors, PA does not in fact donate significant amounts of nitroxyl under physiological conditions (See Zamora, supra).

Several substituted N-hydroxylbenzenesulfonamides have been reported as inhibitors of carbonic anhydrase, with no mention of HNO production (see, (a) Mincione, F.; Menabuoni, L.; Briganti, F; Mincione, G.; Scozzafava, A.; Supuran, C. T. *J. Enzyme Inhibition* 1998, 13, 267-284 and (b) Scozzafava, A.; Supuran, C. T., *J. Med. Chem.* 2000, 43, 3677-3687).

N-hydroxylsulfonamide derivatives as new physiologically useful nitroxyl donors are also described in PCT application No. PCT/US2007/006710 filed Mar. 16, 2007. However, compounds of the formula (I) described therein are not substituted with at least one carboxyl, carboxyl ester, acylamino or sulfonylamino group and compounds of the formula (II) or (III) described therein are not substituted with at least one carbonylamino or sulfonylamino group.

Significant Medical Need

Despite efforts towards the development of new therapies for the treatment of diseases and conditions such as heart failure and ischemia/reperfusion injury, there remains a significant interest in and need for additional or alternative compounds that treat or prevent the onset or severity of these and related diseases or conditions. In particular, there remains a significant medical need for alternative or additional therapies for the treatment of diseases or conditions that are responsive to nitroxyl therapy. New compounds that donate nitroxyl under physiological conditions and methods of using compounds that donate nitroxyl under physiological conditions may thus find use as therapies for treating, preventing and/or delaying the onset and/or development of diseases or conditions responsive to nitroxyl therapy, including heart disease and ischemia/reperfusion injury. Preferably, the therapeutic agents can improve the quality of life and/or prolong the survival time for patients with the disease or condition.

BRIEF SUMMARY OF THE INVENTION

Methods, compounds and compositions for treating and/or preventing the onset or development of diseases or conditions that are responsive to nitroxyl therapy are described. Aromatic and non-aromatic N-hydroxylsulfonamide derivatives that donate nitroxyl under physiological conditions are described. By modifying PA with appropriate substituents, such as electron-withdrawing groups or groups that sterically hinder the sulfonyl moiety, the HNO producing capacity of these derivatives is substantially enhanced under physiological conditions. Significantly, when compared to AS, PA has the capacity for broad substituent modification, enabling optimization of physicochemical and pharmacological properties. Such optimization is reported herein.

In one embodiment, the present invention provides a method of administering to a subject in need thereof, a therapeutically effective amount of a derivative of PA wherein the derivative donates nitroxyl under physiological conditions. In one embodiment, the invention embraces a method of treating or preventing the onset and/or development of a disease or condition that is responsive to nitroxyl therapy, the method comprising administering to an individual in need thereof an N-hydroxylsulfonamide that donates an effective amount of nitroxyl under physiological conditions. Also embraced are methods of treating heart failure or ischemia/reperfusion injury by administering to an individual in need thereof an N-hydroxysulfonamide that donates an effective amount of nitroxyl under physiological conditions.

Kits comprising the compounds are also described, which may optionally contain a second therapeutic agent such as a positive inotropic compound, which may be, e.g., a beta-adrenergic receptor agonist.

Novel compounds that find use in the invention described herein include compounds of the formula (I), (II) or (III):

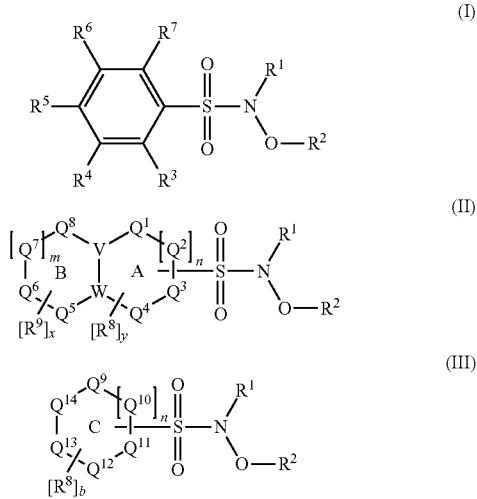

where $R^1$ is H; $R^2$ is H, aralkyl or heterocyclyl; m and n are independently an integer from 0 to 2; x is an integer from 0 to 4 and y is an integer from 0 to 3, provided that at least one of x and y is greater than 0; b is an integer from 1-4; $R^3$, $R^4$, $R^5$, $R^6$ and $R^7$ are independently selected from the group consisting of H, halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, cycloalkoxy, cycloalkylsulfanyl, arylsulfanyl, arylsulfinyl, carboxyl, carboxyl ester, acylamino and sulfonylamino, provided that at least one of $R^3$, $R^4$, $R^5$, $R^6$ and $R^7$ is carboxyl, carboxyl ester, acylamino or sulfonylamino; each $R^8$ and $R^9$ is independently selected from the group consisting of halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, $NH_2$, OH, C(O)OH, C(O)Oalkyl, NHC(O)alkylC(O)OH, C(O)$NH_2$, NHC(O)alkylC(O)alkyl, NHC(O)alkenylC(O)OH, NHC(O)$NH_2$, OalkylC(O)Oalkyl, NHC(O)alkyl, C(=N—OH)$NH_2$, cycloalkoxy, cycloalkylsulfanyl, arylsulfanyl, arylsulfinyl, carbonylamino, and sulfonylamino, provided that: (1) at least one $R^8$ is carbonylamino or sulfonylamino when the compound is of the formula (III) and (2) at least one of $R^8$ and $R^9$ is carbonylamino or sulfonylamino when the compound is of the formula (II); A is a cycloalkyl, heterocycloalkyl, aromatic or heteroaromatic ring containing ring moieties $Q^1$, $Q^2$, $Q^3$ and $Q^4$, which are taken together with V and W to form ring A; B is a cycloalkyl, heterocycloalkyl, aromatic or heteroaromatic ring containing ring moieties $Q^5$, $Q^6$, $Q^7$ and $Q^8$, which are taken together with the V and W to form ring B; V and W are independently C, CH, N or $NR^{10}$; $Q^1$, $Q^2$, $Q^3$, $Q^4$, $Q^5$, $Q^6$, $Q^7$ and $Q^8$ are independently selected from the group consisting of C, $CH_2$, CH, N, $NR^{10}$, O and S; C is a heteroaromatic ring containing ring moieties $Q^9$, $Q^{10}$, $Q^{11}$, $Q^{12}$, $Q^{13}$ and $Q^{14}$ that are independently selected from the group consisting of C, $CH_2$, CH, N, $NR^{10}$, O and S, provided that at least one of $Q^9$, $Q^{10}$, $Q^{11}$, $Q^{12}$, $Q^{13}$ and $Q^{14}$ is N, $NR^{10}$, O or S; and $R^{10}$ is H, alkyl, acyl or sulfonyl. Pharmaceutically acceptable salts of any of the foregoing are also described.

In one variation, the compound is of the formula (I), (II) or (III) where $R^1$ is H; $R^2$ is H; m and n are independently an integer from 0 to 2; x is an integer from 0 to 4 and y is an integer from 0 to 3, provided that at least one of x and y is greater than 0; b is an integer from 1-4; $R^3$, $R^4$, $R^5$, $R^6$ and $R^7$ are independently selected from the group consisting of H, halo, alkylsulfonyl, substituted alkylsulfonyl, N-hydroxylsulfonamidyl, substituted N-hydroxylsulfonamidyl, perhaloalkyl, substituted perhaloalkyl (where one or more halo may be substituted with a substituent), nitro, aryl, substituted aryl, cyano, alkoxy, substituted alkoxy, perhaloalkoxy, substituted perhaloalkoxy, alkyl, substituted alkyl, aryloxy, substituted aryloxy, alkylsulfanyl, substituted alkylsulfanyl, alkylsulfinyl, substituted alkylsulfinyl, heterocycloalkyl, substituted heterocycloalkyl, dialkylamino, substituted dialkylamino, cycloalkoxy, substituted cycloalkoxy, cycloalkylsulfanyl, substituted cycloalkylsulfanyl, arylsulfanyl, substituted arylsulfanyl, arylsulfinyl, substituted arylsulfinyl, carboxyl, carboxyl ester, acylamino and sulfonylamino, provided that at least one of $R^3$, $R^4$, $R^5$, $R^6$ and $R^7$ is carboxyl, carboxyl ester, acylamino or sulfonylamino; each $R^8$ and $R^9$ is independently selected from the group consisting of halo, alkylsulfonyl, substituted alkylsulfonyl, N-hydroxylsulfonamidyl, substituted N-hydroxylsulfonamidyl, perhaloalkyl, substituted perhaloalkyl, nitro, aryl, substituted aryl, cyano, alkoxy, substituted alkoxy, perhaloalkoxy, substituted perhaloalkoxy, alkyl, substituted alkyl, aryloxy, substituted aryloxy, alkylsulfanyl, substituted alkylsulfanyl, alkylsulfinyl, substituted alkylsulfinyl, heterocycloalkyl, substituted heterocycloalkyl, dialkylamino, substituted dialkylamino, $NH_2$, OH, C(O)OH, C(O)Oalkyl, NHC(O)alkylC(O)OH, C(O)$NH_2$, NHC(O)alkylC(O)alkyl, NHC(O)alkenylC(O)OH, NHC(O)$NH_2$, OalkylC(O)Oalkyl, NHC(O)alkyl, C(=N—OH)$NH_2$, cycloalkoxy, substituted cycloalkoxy, cycloalkylsulfanyl, substituted cycloalkylsulfanyl, arylsulfanyl, substituted arylsulfanyl, arylsulfinyl, substituted arylsulfinyl (where any listing of alkyl or alkenyl in the moieties above intends unsubstituted or substituted alkyl or alkenyl), carbonylamino and sulfonylamino, provided that: (1) at least one $R^8$ is carbonylamino or sulfonylamino when the compound is of the formula (III) and (2) at least one of $R^8$ and $R^9$ is carbonylamino or sulfonylamino when the compound is of the formula (II); A is a cycloalkyl, heterocycloalkyl, aromatic or heteroaromatic ring containing ring moieties $Q^1$, $Q^2$, $Q^3$ and $Q^4$, which are taken together with V and W to form ring A; B is a cycloalkyl, heterocycloalkyl, aromatic or heteroaromatic ring containing ring moieties $Q^5$, $Q^6$, $Q^7$ and $Q^8$, which are taken together with the V and W to form ring B; V and W are independently C, CH, N or $NR^{10}$; $Q^1$, $Q^2$, $Q^3$, $Q^4$, $Q^5$, $Q^6$, $Q^7$ and $Q^8$ are independently selected from the group consisting of C, $CH_2$, CH, N, $NR^{10}$, O and S; C is a heteroaromatic ring containing ring moieties $Q^9$, $Q^{10}$, $Q^{11}$, $Q^{12}$, $Q^{13}$ and $Q^{14}$ that are independently selected from the group consisting of C, $CH_2$, CH, N, $NR^{10}$, O and S, provided that at least one of $Q^9$, $Q^{10}$, $Q^{11}$, $Q^{12}$, $Q^{13}$ and $Q^{14}$ is N, $NR^{10}$, O or S; and $R^{10}$ is H, alkyl, acyl or sulfonyl. Pharmaceutically acceptable salts of any of the foregoing are also described.

Methods of using the compounds detailed herein are also described, including a method of treating, preventing or delaying the onset or development of a disease or condition that is responsive to nitroxyl therapy, comprising administering to an individual in need thereof a compound of the invention that donates nitroxyl under physiological conditions or a pharmaceutically acceptable salt thereof.

Pharmaceutical compositions comprising a compound of the invention are disclosed, such as pharmaceutical compositions that are amenable to intravenous injection. Kits comprising a compound of the invention and instructions for use are also described.

BRIEF DESCRIPTION OF THE DRAWINGS

FIG. 1 illustrates the nitrous oxide evolved from Compounds 1-5 as a percent of Angeli's Salt and the mole percent of $N_2O$ generated per mole of sample for compounds 1-5.

DETAILED DESCRIPTION OF THE INVENTION

Definitions

Unless clearly indicated otherwise, the following terms as used herein have the meanings indicated below.

Use of the terms "a", "an" and the like refers to one or more.

"Aralkyl" refers to a residue in which an aryl moiety is attached to the parent structure via an alkyl residue. Examples include benzyl (—$CH_2$-Ph), phenethyl (—$CH_2CH_2$Ph), phenylvinyl (—CH=CH-Ph), phenylallyl and the like.

"Acyl" refers to and includes the groups —C(O)H, —C(O)alkyl, —C(O)substituted alkyl, —C(O)alkenyl, —C(O)substituted alkenyl, —C(O)alkynyl, —C(O)substituted alkynyl, —C(O)cycloalkyl, —C(O)substituted cycloalkyl, —C(O)aryl, —C(O)substituted aryl, —C(O)heteroaryl, —C(O)substituted heteroaryl, —C(O)heterocyclic, and —C(O)substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein or otherwise known in the art.

"Heterocyclyl" or "Heterocycloalkyl" refers to a cycloalkyl residue in which one to four of the carbons is replaced by a heteroatom such as oxygen, nitrogen or sulfur. Examples of heterocycles whose radicals are heterocyclyl groups include tetrahydropyran, morpholine, pyrrolidine, piperidine, thiazolidine, oxazole, oxazoline, isoxazole, dioxane, tetrahydrofuran and the like. A specific example of a heterocyclyl residue is tetrahydropyran-2-yl.

"Substituted heterocyclo" or "substituted heterocylcoalkyl" refers to an heterocyclyl group having from 1 to 5 substituents. For instance, a heterocyclyl group substituted with 1 to 5 groups such as halo, nitro, cyano, oxo, aryl, alkoxy, alkyl, acyl, acylamino, amino, hydroxyl, carboxyl, carboxylalkyl, thiol, thioalkyl, heterocyclyl, —OS(O)$_2$-alkyl, and the like is a substituted alkyl. A particular example of a substituted heterocylcoalkyl is N-methylpiperazino.

"Alkyl" intends linear hydrocarbon structures having 1 to 20 carbon atoms, preferably 1 to 12 carbon atoms and more preferably 1 to 8 carbon atoms. Alkyl groups of fewer carbon atoms are embraced, such as so-called "lower alkyl" groups having 1 to 4 carbon atoms. "Alkyl" also intends branched or cyclic hydrocarbon structures having 3 to 20 carbon atoms, preferably 3 to 12 carbon atoms and more preferably 3 to 8 carbon atoms. For any use of the term "alkyl," unless clearly indicated otherwise, it is intended to embrace all variations of alkyl groups disclosed herein, as measured by the number of carbon atoms, the same as if each and every alkyl group was explicitly and individually listed for each usage of the term.

For instance, when a group such as $R^3$ may be an "alkyl," intended is a $C_1$-$C_{20}$ alkyl or a $C_1$-$C_{12}$ alkyl or a $C_1$-$C_5$ alkyl or a lower alkyl or a $C_2$-$C_{20}$ alkyl or a $C_3$-$C_{12}$ alkyl or a $C_3$-$C_8$ alkyl. The same is true for other groups listed herein, which may include groups under other definitions, where a certain number of atoms is listed in the definition. When the alkyl group is cyclic, it may also be referred to as a cycloalkyl group and have e.g., 3 to 20 annular carbon atoms, preferably 3 to 12 annular carbon atoms and more preferably 3 to 8 annular carbon atoms. When an alkyl residue having a specific number of carbons is named, all geometric isomers having that number of carbons are intended to be encompassed; thus, for example, "butyl" is meant to include n-butyl, sec-butyl, iso-butyl and t-butyl; "propyl" includes n-propyl and iso-propyl. Examples of alkyl groups include methyl, ethyl, n-propyl, i-propyl, t-butyl, n-heptyl, octyl, cyclopentyl, cyclopropyl, cyclobutyl, norbornyl, and the like. One or more degrees of unsaturation may occur in an alkyl group. Thus, an alkyl group also embraces alkenyl and alkynyl residues. "Alkenyl" is understood to refer to a group of 2 or more carbon atoms, such as 2 to 10 carbon atoms and more preferably 2 to 6 carbon atoms and having at least 1 and preferably from 1-2 sites of alkenyl unsaturation. Examples of an alkenyl group include —C=$CH_2$, —$CH_2$CH=$CHCH_3$ and —$CH_2$CH=CH—CH=$CH_2$. "Alkynyl" refers to alkynyl group preferably having from 2 to 10 carbon atoms and more preferably 3 to 6 carbon atoms and having at least 1 and preferably from 1-2 sites of alkynyl unsaturation, such as the moiety —C≡CH. Alkyl is also used herein to denote an alkyl residue as part of a larger functional group and when so used, is taken together with other atoms to form another functional group. For instance, reference to —C(O)Oalkyl intends an ester functional group, where the alkyl portion of the moiety may be any alkyl group, and provide by way of example only, the functional group —C(O)O$CH_3$, —C(O)(O)CH=$CH_2$ and the like. Another example of an alkyl group as part of a larger structure includes the residue —NHC(O)alkylC(O)OH, which e.g., may be NHC(O)$CH_2CH_2$C(O)OH when alkyl is —$CH_2CH_2$—.

"Substituted alkyl" refers to an alkyl group having from 1 to 5 substituents. For instance, an alkyl group substituted with a group such as halo, nitro, cyano, oxo, aryl, alkoxy, acyl, acylamino, amino, hydroxyl, carboxyl, carboxylalkyl, thiol, thioalkyl, heterocyclyl, —OS(O)$_2$-alkyl, and the like is a substituted alkyl. Likewise, "substituted alkenyl" and "substituted alkynyl" refer to alkenyl or alkynyl groups having 1 to 5 substituents.

As used herein the term "substituent" or "substituted" means that a hydrogen radical on a compound or group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=Nalkyl). In other embodiments, substituents on any group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) can be at any atom of that group (such as on a carbon atom of the primary carbon chain of a substituted alkyl group or on a substituent already present on a substituted alkyl group) or at any atom of, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy. Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{11}$, $SR^{11}$, $S(O)_2OR^{11}$, $NR^{11}R^{12}$, $C_1$-$C_2$perfluoroalkyl, $C_1$-$C_2$ perfluoroalkoxy, 1,2-methylenedioxy, (=O), (=S), (=$NR^{11}$), C(O)$OR^{11}$, C(O)$R^{11}R^{12}$, OC(O)$NR^{11}R^{12}$, $NR^{11}$C(O)$NR^{11}R^{12}$, C($NR^{12}$)$NR^{11}R^{12}$, $NR^{11}$C($NR^{12}$)$NR^{11}R^{12}$, $S(O)_2NR^{11}R^{12}R^{13}$, C(O)H, C(O)$R^{13}$, $NR^{11}$C(O)$R^{13}$, Si($R^{11}$)$_3$, OSi($R^{11}$)$_3$, Si(OH)$_2R^{11}$, B(OH)$_2$, P(O)(O$R^{11}$)$_2$, S(O)$R^{13}$, or $S(O)_2R^{13}$. Each $R^{11}$ is independently hydrogen, $C_1$-$C_6$ alkyl optionally substituted with cycloalkyl, aryl, heterocyclyl, or heteroaryl. Each $R^{12}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{13}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{11}$, $R^{12}$ and $R^{13}$ can optionally be substituted with halogen, CN, $C_1$-$C_4$ alkyl, OH, $C_1$-$C_4$ alkoxy, COOH, C(O)O$C_1$-$C_4$ alkyl, $NH_2$, $C_1$-$C_4$ alkylamino, or $C_1$-$C_4$ dialkylamino. Substituents can also be "electron-withdrawing groups."

"Electron withdrawing group" refers to groups that reduce electron density of the moiety to which they are attached (relative to the density of the moiety without the substituent). Such groups include, for example, F, Cl, Br, I, —CN, —$CF_3$, —$NO_2$, —SH, —C(O)H, —C(O)alkyl, —C(O)Oalkyl, —C(O)OH, —C(O)Cl, —S(O)$_2$OH, —S(O)$_2$NHOH, —$NH_3$ and the like.

"Halo" refers to fluorine, chlorine, bromine or iodine.

"Alkylsulfonyl" refers to groups —$SO_2$alkyl and —$SO_2$substituted alkyl, which includes the residues —$SO_2$cycloalkyl, —$SO_2$substituted cycloalkyl, —$SO_2$alkenyl, —$SO_2$substituted alkenyl, —$SO_2$alkynyl, —$SO_2$substituted alkynyl, where alkyl, substituted alkyl, alkenyl, substituted alkenyl, alkynyl, substituted alkynyl, cycloalkyl and substituted cycloalkyl are as defined herein.

"N-hydroxylsulfonamidyl" refers to —S(O)$_2$NROH, where R is H or alkyl.

"Perhaloalkyl" refers to an alkyl group where each H of the hydrocarbon is replaced with F. Examples of perhalo groups include —$CF_3$ and —$CF_2CF_3$.

"Aryl" intends a monocyclic, bicyclic or tricyclic aromatic ring. An aryl group is preferably a 5- or 6-membered aromatic or heteroaromatic ring containing 0-3 annular heteroatoms selected from O, N, or S; a bicyclic 9- or 10-membered aromatic or heteroaromatic ring system (meaning the ring system has 9 or 10 annular atoms) containing 0-3 annular heteroatoms selected from O, N, or S; or a tricyclic 13- or 14-membered aromatic or heteroaromatic ring system (meaning the ring system has 13 or 14 annular atoms) containing 0-3 annular heteroatoms selected from O, N, or S. Examples of groups whose radicals are aryl groups include e.g., benzene, naphthalene, indane, tetralin, imidazole, pyridine, indole, thiophene, benzopyranone, thiazole, furan, benzimidazole, benzoxazole, benzthiazole, quinoline, isoquinoline, quinoxaline, pyrimidine, pyrazine, tetrazole and pyrazole.

"Substituted aryl" refers to a group having from 1 to 3 substituents. For instance, an aryl group substituted with 1 to 3 groups such as halo, nitro, cyano, oxo, aryl, alkoxy, alkyl, acyl, acylamino, amino, hydroxyl, carboxyl, carboxylalkyl, thiol, thioalkyl, heterocyclyl, —OS(O)$_2$-alkyl, and the like is a substituted aryl.

"Alkoxy" refers to an alkyl group that is connected to the parent structure through an oxygen atom (—O-alkyl). When a cycloalkyl group is connected to the parent structure through an oxygen atom, the group may also be referred to as a cycloalkoxy group. Examples include methoxy, ethoxy, propoxy, isopropoxy, cyclopropyloxy, cyclohexyloxy and the like. A "perhaloalkoxy" intends a perhaloalkyl group attached to the parent structure through an oxygen, such as the residue —O—$CF_3$.

"Aryloxy" refers to an aryl group that is connected to the parent structure through an oxygen atom (—O-aryl), which by way of example includes the residues phenoxy, naphthoxy, and the like. "Substituted aryloxy" refers to a substituted aryl group connected to the parent structure through an oxygen atom (—O-substituted aryl).

"Alkylsulfanyl" refers to an alkyl group that is connected to the parent structure through a sulfur atom (—S-alkyl) and refers to groups —S-alkyl and —S-substituted alkyl, which includes the residues —S-cycloalkyl, —S-substituted cycloalkyl, —S-alkenyl, —S-substituted alkenyl, —S-alkynyl, —S-substituted alkynyl, where alkyl, substituted alkyl, alkenyl, substituted alkenyl, alkynyl, substituted alkynyl, cycloalkyl and substituted cycloalkyl are as defined herein. When a cycloalkyl group is connected to the parent structure through an sulfur atom, the group may also be referred to as a cycloalkylsulfanyl group. By way of example, alkylsulfanyl includes —S—CH($CH_3$), —S—$CH_2CH_3$ and the like.

"Alkylsulfinyl" refers to an alkyl group that is connected to the parent structure through a S(O) moiety and refers to groups —S(O)alkyl and —S(O)substituted alkyl, which includes the residues —S(O)cycloalkyl, —S(O)substituted cycloalkyl, —S(O)alkenyl, —S(O)substituted alkenyl, —S(O)alkynyl, —S(O)substituted alkynyl, where alkyl, substituted alkyl, alkenyl, substituted alkenyl, alkynyl, substituted alkynyl, cycloalkyl and substituted cycloalkyl are as defined herein. By way of example, alkylsulfinyl includes the residues —S(O)CH(CH$_3$), —S(O)CH$_3$, —S(O)cyclopentane and the like.

"Arylsulfinyl" refers to an aryl group that is connected to the parent structure through a S(O) moiety, which by way of example includes the residue —S(O)Ph.

"Dialkylamino" refers to the group —NR$_2$ where each R is an alkyl group. Examples of dialkylamino groups include —N(CH$_3$)$_2$, —N(CH$_2$CH$_2$CH$_2$CH$_3$)$_2$, and N(CH$_3$)(CH$_2$CH$_2$CH$_2$CH$_3$).

"Carboxyl" refers to —C(O) OH.

"Carboxyl ester" as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Acylamino" refers to the group —C(O)NR$_a$R$_b$ where each R$_a$ and R$_b$ group is independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring. An examples of an acylamino moiety includes —C(O)morpholino.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic where R is hydrogen or alkyl, or —SO$_2$NR$_2$, where the two R groups are taken together and with the nitrogen atom to which they are attached to form a heterocyclic or substituted heterocyclic ring.

"Carbonylamino" refers to the groups —CONH$_2$, —CONR-alkyl, —CONR-substituted alkyl, —CONR-alkenyl, —CONR-substituted alkenyl, —CONR-alkynyl, —CONR-substituted alkynyl, —CONR-aryl, —CONR-substituted aryl, —CONR-heteroaryl, —CONR-substituted heteroaryl, —CONR-heterocyclic, and —CONR-substituted heterocyclic where R is hydrogen or alkyl, or —CONR$_2$, where the two R groups are taken together and with the nitrogen atom to which they are attached to form a heterocyclic or substituted heterocyclic ring.

"Pharmaceutically acceptable salt" refers to pharmaceutically acceptable salts of a compound described herein, such as a compound of Formula (I), (II) or (III) or other nitroxyl donor of the invention, which salts may be derived from a variety of organic and inorganic counter ions well known in the art and include, by way of example only, sodium, potassium, calcium, magnesium, ammonium, tetraalkylammonium, and the like; when the molecule contains a basic functionality, salts of organic or inorganic acids, such as hydrochloride, hydrobromide, tartrate, mesylate, acetate, maleate, oxalate and the like. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt may be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. A salt may also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

Unless clearly indicated otherwise, "an individual" as used herein intends a mammal, including but not limited to a human.

The term "effective amount" intends such amount of a compound or a pharmaceutically acceptable salt thereof, which in combination with its parameters of efficacy and toxicity, as well as based on the knowledge of the practicing specialist should be effective in a given therapeutic form. As is understood in the art, an effective amount may be in one or more doses.

As used herein, "treatment" or "treating" is an approach for obtaining a beneficial or desired result, including clinical results. For purposes of this invention, beneficial or desired results include but are not limited to inhibiting and/or suppressing the onset and/or development of a disease or condition that is responsive to nitroxyl therapy or reducing the severity of such disease or condition, such as reducing the number and/or severity of symptoms associated with the disease or condition, increasing the quality of life of those suffering from the disease or condition, decreasing the dose of other medications required to treat the disease or condition, enhancing the effect of another medication an individual is taking for the disease or condition and prolonging survival of individuals having the disease or condition. The disease or condition may be a cardiovascular disease or condition, which includes, but is not limited to, coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Related symptoms that may be alleviated by the methods herein include shortness of breath, fatigue, swollen ankles or legs, angina, loss of appetite, weight gain or loss, associated with aforementioned diseases or disorders. The disease or condition may involve ischemia/reperfusion injury.

As used herein, "preventing" refers to reducing the probability of developing a disorder or condition in an individual who does not have, but is at risk of developing a disorder or condition."

An individual "at risk" may or may not have a detectable disease or condition, and may or may not have displayed a detectable disease or condition prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Nitroxyl" refers to the species HNO.

As used herein, a compound is a "nitroxyl donor" if it donates nitroxyl under physiological conditions. As used herein, nitroxyl donors of the invention may alternatively be referred to as "a compound" or "the compound." Preferably, the nitroxyl donor is capable of donating an effective amount of nitroxyl in vivo and has a safety profile indicating the compound would be tolerated by an individual in the amount necessary to achieve a therapeutic effect. One of ordinary skill in the art would be able to determine the safety of administering particular compounds and dosages to live subjects. One of skill in the art may also determine whether a compound is a nitroxyl donor by evaluating whether it releases HNO under physiological conditions. Compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in water, in a sealed container. After sufficient time for disassociation has elapsed, such as from several minutes to several hours, the headspace gas is withdrawn and analyzed to determine its composition, such as by gas chromatography and/or mass spectroscopy. If the gas $N_2O$ is formed (which occurs by HNO dimerization), the test is positive for nitroxyl donation and the compound is a nitroxyl donor. The level of nitroxyl donating ability may be expressed as a percentage of a compound's theoretical maximum. A compound that donates a "significant level of nitroxyl" intends a compound that donates 40% or more or 50% or more of its theoretical maximum amount of nitroxyl. In one variation, the compounds for use herein donate 60% or more of the theoretical maximum amount of nitroxyl. In another variation, the compounds for use herein donate 70% or more of the theoretical maximum amount of nitroxyl. In another variation, the compounds for use herein donate 80% or more of the theoretical maximum amount of nitroxyl. In another variation, the compounds for use herein donate 90% or more of the theoretical maximum amount of nitroxyl. In yet another variation, the compounds for use herein donate between about 70% and about 90% of the theoretical maximum amount of nitroxyl. In yet another variation, the compounds for use herein donate between about 85% and about 95% of the theoretical maximum amount of nitroxyl. In yet another variation, the compounds for use herein donate between about 90% and about 95% of the theoretical maximum amount of nitroxyl. Compounds that donate less than 40% or less than 50% of their theoretical amount of nitroxyl are still nitroxyl donors and may be used in the invention disclosed herein. A compound that donates less than 50% of the theoretical amount of nitroxyl may be used in the methods described, and may require higher dosing levels as compared to compounds that donate a significant level of nitroxyl. Nitroxyl donation also can be detected by exposing the test compound to metmyoglobin ($Mb^{3+}$). Nitroxyl reacts with $Mb^{3+}$ to form an $Mb^{2+}$—NO complex, which can be detected by changes in the ultraviolet/visible spectrum or by Electron Paramagnetic Resonance (EPR). The $Mb^{2+}$—NO complex has an EPR signal centered around a g-value of about 2. Nitric oxide, on the other hand, reacts with $Mb^{3+}$ to form an $Mb^{3+}$—NO complex that is EPR silent. Accordingly, if the candidate compound reacts with $Mb^{3+}$ to form a complex detectable by common methods such as ultraviolet/visible or EPR, then the test is positive for nitroxyl donation. Testing for nitroxyl donation may be performed at physiologically relevant pH.

A "positive inotrope" as used herein is an agent that causes an increase in myocardial contractile function. Such an agent includes a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 describes a dobutamine prodrug that can be administered orally. One of ordinary skill in the art would be able to determine if a compound is capable of causing positive inotropic effects and also additional beta-agonist compounds. In particular embodiments, the beta-receptor agonist is selective for the beta-1 receptor. However, in other embodiments the beta-agonist is selective for the beta-2 receptor, or is not selective for any particular receptor.

Diseases or conditions that are "responsive to nitroxyl therapy" intends any disease or condition in which administration of a compound that donates an effective amount of nitroxyl under physiological conditions treats and/or prevents the disease or condition, as those terms are defined herein. A disease or condition whose symptoms are suppressed or diminished upon administration of nitroxyl donor is a disease or condition responsive to nitroxyl therapy. Non-limiting examples of diseases or conditions that are responsive to nitroxyl therapy include coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Other cardiovascular diseases or conditions are also intended, as are diseases or conditions that implicate ischemia/reperfusion injury.

N-Hydroxysulfonamide Compounds

The compounds of this invention and for use in the methods described herein include N-hydroxylsulfonamides that donate nitroxyl under physiological conditions. Preferably, the compounds predominately donate nitroxyl under physiological conditions, meaning that a compound that donates both nitroxyl and nitric oxide under physiological conditions donates more nitroxyl than nitric oxide. Preferably, the compounds for use herein do not donate significant levels of nitric oxide under physiological conditions. Most preferably, the compounds for use herein donate significant levels of nitroxyl under physiological conditions.

In one embodiment, the invention embraces a compound of the formula (I):

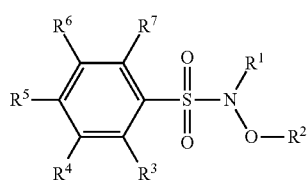

where $R^1$ is H; $R^2$ is H, aralkyl or heterocyclyl; $R^3$, $R^4$, $R^5$, $R^6$ and $R^7$ are independently selected from the group consisting of H, halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, cycloalkoxy, cycloalkylsulfanyl, arylsulfanyl, arylsulfinyl, carboxyl, carboxyl ester, acylamino and sulfonylamino, provided that at least one of $R^3$, $R^4$, $R^5$, $R^6$ and $R^7$ is carboxyl, carboxyl ester, acylamino or sulfonylamino.

In another embodiment, the compound is of the formula (I) where $R^1$ is H; $R^2$ is H, aralkyl or heterocyclyl; $R^4$, $R^5$ and $R^6$ are independently H, halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, cycloalkoxy, cycloalkylsulfanyl, arylsulfanyl, arylsulfinyl, carboxyl, carboxyl ester, acylamino or sulfonylamino; at least one of $R^3$ and $R^7$ is an electron withdrawing group or a group that sterically hinders the sulfonyl moiety, provided that at least one of $R^3$, $R^4$, $R^5$, $R^6$ and $R^7$ is carboxyl, carboxyl ester, acylamino or sulfonylamino. In one variation, at least one of $R^3$ or $R^7$ is an electron withdrawing group. In another variation, both $R^3$ and $R^7$ are electron withdrawing groups. In another variation, at least one of $R^3$ or $R^7$ is a group that sterically hinders the sulfonyl moiety of compound (I). In one variation, at least one of $R^3$ or $R^7$ is a branched alkyl group, such as i-propyl or t-butyl. In another variation, both $R^3$ and $R^7$ are alkyl groups provided that one of the alkyl groups is a branched alkyl group, such as when both groups are isopropyl or when one group is ethyl and the other is sec-butyl. In one variation, one of $R^3$ and $R^7$ is an electron withdrawing group and the $R^3$ or $R^7$ that is not an electron withdrawing group is an alkyl group, which may be a branched alkyl group such as isopropyl.

Also embraced is a compound of the formula (I) where $R^1$ is H; $R^2$ is H, benzyl or tetrahydropyran-2-yl; $R^3$, $R^4$, $R^5$, $R^6$ and $R^7$ are independently selected from the group consisting of H, Cl, F, I, Br, $SO_2CH_3$, $SO_2NHOH$, $CF_3$, $NO_2$, phenyl, CN, $OCH_3$, $OCF_3$, t-Bu, 4-nitrophenyloxy (OPh4-$NO_2$), propane-2-thiyl ($SCH(CH_3)_2$), propane-2-sulfinyl ($S(O)CH(CH_3)_2$), morpholino, N-methyl-piperazino, dimethylamino, piperidino, cyclohexyloxy, cyclopentylsulfanyl, phenylsulfanyl, phenylsulfinyl, carboxyl, carboxyl ester, acylamino or sulfonylamino provided that at least one of $R^3$, $R^4$, $R^5$, $R^6$ and $R^7$ is carboxyl, carboxyl ester, acylamino or sulfonylamino.

For any of the variations described for formula (I), included are variations of formula (I) where $R^1$ is H and $R^2$ is H, benzyl or tetrahydropyran-2-yl. In one variation, the compound is of the formula (I) where at least two of $R^3$, $R^4$, $R^5$, $R^6$ and $R^7$ are halo, such as the compound of formula (I) where $R^5$ is halo (such as F or Br) and one of $R^3$ and $R^7$ is halo (such as Br, or Cl) or where both $R^3$ and $R^7$ or both $R^3$ and $R^4$ are halo (such as when both are Cl or both are F or one is Cl and one is F), and the remaining substituents are as described in the variations above. In one variation, the compound is of the formula (I) where at least one of $R^3$, $R^4$, $R^5$, $R^6$ and $R^7$ is —S(O)$_2$alkyl, such as when one of $R^3$ or $R^7$ is —S(O)$_2CH_3$. In one variation, the compound is of the formula (I) where at least one of $R^3$, $R^5$ and $R^7$ is a perhaloalkyl, such as when $R^3$ is $CF_3$ or when $R^3$ and $R^5$ are $CF_3$. In one variation, the compound is of the formula (I) where $R^5$ is $CF_3$ and at least one of $R^3$ and $R^7$ is other than H, such as when $R^5$ is $CF_3$ and $R^3$ is $NO_2$ or Cl. In one variation, the compound is of the formula (I) where at least one of $R^3$, $R^4$, $R^5$, $R^6$ and $R^7$ is an aryl group, such as when at least one of $R^3$ and $R^7$ is an aryl group, such as phenyl. In one variation, the compound is of the formula (I) where at least one of $R^3$, $R^4$, $R^5$, $R^6$ and $R^7$ is a heterocyclyl group, such as when at least one of $R^3$, $R^5$ and $R^7$ is a heterocyclyl group or substituted heterocylco group, such as morpholino, N-methyl, piperizino and piperidino. In one variation, the compound is of the formula (I) where at least one of $R^3$, $R^4$, $R^5$, $R^6$ and $R^7$ is a cycloalkoxy or cycloalkylsulfanyl group such as when at least one of $R^3$, $R^5$ and $R^7$ is a cyclohexyloxy, cyclopentyloxy, cyclohexylsulfanyl or cyclopentylsulfanyl group. In one variation, the compound is of the formula (I) where at least one of $R^3$, $R^4$, $R^5$, $R^6$ and $R^7$ is an arylsulfanyl or arylsulfinyl group, such as when at least one of $R^3$, $R^5$ and $R^7$ is a phenylsulfanyl or phenylsulfinyl group.

For any of the variations described for formula (I), included are variations of formula (I) where at least one of $R^3$, $R^4$, $R^5$, $R^6$ and $R^7$ is carboxyl. In one such variation, $R^4$ is carboxyl, $R^3$, $R^5$ and $R^6$ are H and $R^7$ is H or halo. In a particular variation, $R^4$ is carboxyl, $R^3$, $R^5$ and $R^6$ are H, $R^7$ is H or halo and $R^1$ and $R^2$ are H. For any of the variations described for formula (I), included are variations of formula (I) where at least one of $R^3$, $R^4$, $R^5$, $R^6$ and $R^7$ is —COO-alkyl. In one such variation, $R^3$ is —COO-alkyl and $R^4$, $R^5$, $R^6$ and $R^7$ are H. In a particular variation, $R^3$ is —COO-alkyl, $R^4$, $R^5$, $R^6$ and $R^7$ are H and $R^1$ and $R^2$ are H. In another variation, $R^4$ is —COO-alkyl, one of $R^6$ and $R^7$ is —$SR^{11}$, aryl, —$OR^{11}$, nitro, cyano, acyl, —S(O)$_2$NHOH, sulfonylamino, $C_1$-$C_2$perfluoroalkyl, lower alkyl or amino and the $R^6$ or $R^7$ that is not $SR^{11}$, aryl, —$OR^{11}$, nitro, cyano, acyl, —S(O)$_2$NHOH, sulfonylamino, $C_1$-$C_2$perfluoroalkyl, lower alkyl or amino is hydrogen. In another variation, $R^4$ is —COO-alkyl, one of $R^6$ and $R^7$ is —$SR^{11}$, aryl, —$OR^{11}$, nitro, cyano, acyl, —S(O)$_2$NHOH, sulfonylamino, $C_1$-$C_2$perfluoroalkyl, lower alkyl or amino and the $R^6$ or $R^7$ that is not —$SR^{11}$, aryl, —$OR^{11}$, nitro, cyano, acyl, —S(O)$_2$NHOH, sulfonamino, $C_1$-$C_2$perfluoroalkyl, lower alkyl or amino is hydrogen, and $R^1$, $R^2$, $R^3$ and $R^5$ are hydrogen. For any of the variations described for formula (I), included are variations of formula (I) where at least one of $R^3$, $R^4$, $R^5$, $R^6$ and $R^7$ is —COO-substituted alkyl. In one such variation, $R^4$ is —COO-substituted alkyl, $R^3$, $R^5$ and $R^6$ are H and $R^7$ is halo. In a particular variation, $R^4$ is —COO-substituted alkyl, $R^7$ is halo, $R^3$, $R^5$ and $R^6$ are H and $R^1$ and $R^2$ are H. For any of the variations described for formula (I), included are variations of formula (I) where at least one of $R^3$, $R^4$, $R^5$, $R^6$ and $R^7$ is —C(O)NH$_2$. For any of the variations described for formula (I), included are variations of formula (I) where at least one of $R^3$, $R^4$, $R^5$, $R^6$ and $R^7$ is —C(O) NR$_a$R$_b$ where R$_a$ is hydrogen and R$_b$ is alkyl. In one such variation, $R^4$ is —C(O)NR$_a$R$_b$ where R$_a$ is hydrogen, R$_b$ is a lower alkyl, $R^3$, $R^5$ and $R^6$ are H and $R^7$ is halo. In a particular variation, $R^4$ is —C(O)NR$_a$R$_b$ where R$_a$ is hydrogen, R$_b$ is lower alkyl, $R^3$, $R^5$ and $R^6$ are H and $R^7$ is halo and $R^1$ and $R^2$ are H. In a particular variation, R$_b$ is a $C_2$-$C_4$ alkyl, such as ethyl, propyl or butyl. In another variation, R$_b$ is a branched lower alkyl, e.g., isopropyl or isobutyl. For any of the variations described for formula (I), included are variations of formula (I) where at least one of $R^3$, $R^4$, $R^5$, $R^6$ and $R^7$ is —C(O) $NR_aR_b$ where $R_a$ is alkyl, substituted alkyl or hydrogen and $R_b$ is substituted alkyl. In one such variation, $R^4$ is —C(O)$NR_aR_b$ where $R_a$ is alkyl, substituted alkyl or hydrogen, $R_b$ is substituted alkyl, $R^3$, $R^5$ and $R^6$ are H and $R^7$ is halo. In a particular variation, $R^4$ is —C(O)$NR_aR_b$ where $R_a$ is alkyl, substituted alkyl or hydrogen, $R_b$ is substituted alkyl, $R^3$, $R^5$ and $R^6$ are H and $R^7$ is halo and $R^1$ and $R^2$ are H. In still another variation, $R^4$ is —C(O)$NR_aR_b$ where $R_a$ is lower alkyl, substituted lower alkyl or hydrogen, $R_b$ is substituted lower alkyl, $R^3$, $R^5$ and $R^6$ are H and $R^7$ is halo. When $R_b$ is a substituted lower alkyl group, in one variation it is a lower alkyl substituted with hydroxyl, carboxyl, amino or alkoxy group. For example, the invention embraces compounds where $R^4$ is —C(O)$NR_aR_b$ wherein $R_a$ is hydrogen, methyl, ethyl, or a lower alkyl substituted with hydroxyl or alkoxy group, $R_b$ is a lower alkyl substituted with hydroxyl, carboxyl, amino or alkoxy group, $R^3$, $R^5$ and $R^6$ are H and $R^7$ is halo; in a further variation $R^1$ and $R^2$ are H. For any of the variations described for formula (I), included are variations of formula (I) where at least one of $R^3$, $R^4$, $R^5$, $R^6$ and $R^7$ is —C(O)$NR_aR_b$ where $R_a$ and $R_b$ are independently alkyl. In one such variation, $R^4$ is —C(O)$NR_aR_b$ where $R_a$ and $R_b$ are independently alkyl, $R^3$, $R^5$ and $R^6$ are H and $R^7$ is halo. In another variation, $R^4$ is —C(O)$NR_aR_b$ where $R_a$ and $R_b$ are independently alkyl, $R^3$ and $R^5$ are hydrogen and one of $R^6$ and $R^7$ is —$SR^{11}$, aryl, —$OR^{11}$, nitro, cyano, acyl, —$S(O)_2NHOH$, sulfonamino, $C_1$-$C_2$perfluoroalkyl, lower alkyl or amino and the $R^6$ or $R^7$ that is not —$SR^{11}$, aryl, —$OR^{11}$, nitro, cyano, acyl, —$S(O)_2NHOH$, sulfonamino, $C_1$-$C_2$perfluoroalkyl, lower alkyl or amino is hydrogen. In a particular variation, $R^4$ is —C(O)$NR_aR_b$ where $R_a$ and $R_b$ are independently alkyl, $R^3$, $R^5$ and $R^6$ are H and $R^7$ is halo and $R^1$ and $R^2$ are H. $R_a$ and $R_b$ may be the same or different, e.g., $R_a$ and $R_b$ in one variation are both methyl or ethyl. For any of the variations described for formula (I), included are variations of formula (I) where at least one of $R^3$, $R^4$, $R^5$, $R^6$ and $R^7$ is —C(O)$NR_aR_b$ where $R_a$ and $R_b$ are taken together with the nitrogen to which they are attached to form a heterocyclic or substituted heterocyclic ring. In one such variation, $R^4$ is —C(O)$NR_aR_b$ where $R_a$ and $R_b$ are taken together with the nitrogen to which they are attached to form a heterocyclic or substituted heterocyclic ring. In another variation, $R^4$ is —C(O)$NR_aR_b$ where $R_a$ and $R_b$ are taken together with the nitrogen to which they are attached to form a heterocyclic or substituted heterocyclic ring, $R^3$, $R^5$ and $R^6$ are H and $R^7$ is halo. In a particular variation, $R^4$ is —C(O)$NR_aR_b$ where $R_a$ and $R_b$ are taken together with the nitrogen to which they are attached to form a heterocyclic or substituted heterocyclic ring, $R^3$, $R^5$ and $R^6$ are H and $R^7$ is halo and $R^1$ and $R^2$ are H. In one variation, $R_a$ and $R_b$ are taken together with the nitrogen to which they are attached to form a heterocyclic ring, such as morpholino. In any variation herein where $R^4$ is —C(O)$NR_aR_b$, in a particular variation, $R_a$ and $R_b$ are taken together with the nitrogen to which they are attached to form a heterocyclic ring selected from piperazinyl, azetidinyl, pyrrolidinyl, piperidinyl, thiomorpholinyl and morpholinyl. In any variation herein where $R^4$ is —(O)$NR_aR_b$, in a particular variation, $R_a$ and $R_b$ are taken together with the nitrogen to which they are attached to form a heterocyclic ring substituted with 1 or 2 moieties selected from lower alkyl, carboxylester, acyl, halo, amino, hydroxyl, substituted lower alkyl, oxo and alkoxy. For example, in any variation herein where $R^4$ is —C(O)$NR_aR_b$, in a particular variation, $R_a$ and $R_b$ are taken together with the nitrogen to which they are attached to form a substituted heterocyclic ring selected from 2,6-dimethylpiperaz-4-yl, 1-isopropylpiperaz-4-yl, 1-(piperazin-4-yl)ethanone, tert-butyl piperaz-4-yl-1-carboxylate, 4-fluoropiperidyl, 4,4-difluoropiperidyl, 4-aminopiperidyl, 4-hydroxypiperidyl, 4-oxopiperidinyl, 4-methoxypiperidyl, 4-(2-hydroxyethyl)piperidyl, 2-(piperid-4-yl)-ethoxyethanol, 3-hydroxy-azetidinyl, 2-oxo-piperazin-4-yl and 1-methyl-2-oxo-piperazin-4-yl. For any of the variations described for formula (I), included are variations of formula (I) where at least one of $R^3$, $R^4$, $R^5$, $R^6$ and $R^7$ is —$SO_2NH_2$. For any of the variations described for formula (I), included are variations of formula (I) where at least one of $R^3$, $R^4$, $R^5$, $R^6$ and $R^7$ is —$SO_2$NR-alkyl where R is hydrogen. For any of the variations described for formula (I), included are variations of formula (I) where at least one of $R^3$, $R^4$, $R^5$, $R^6$ and $R^7$ is —$SO_2$NR-alkyl where R is alkyl. In a particular variation, $R^4$ is —$SO_2$NR-alkyl where R is alkyl and $R^3$, $R^5$, $R^6$ and $R^7$ are hydrogen. For example, in one variation, $R^4$ is —$SO_2N(lower alkyl)_2$ and $R^3$, $R^5$, $R^6$ and $R^7$ are hydrogen, where the lower alkyl substituents may be the same or different, e.g., $R^4$ may be —$SO_2N(Et)_2$ or —$SO_2N(Et)(Me)$. For any of the variations described for formula (I), included are variations of formula (I) where at least one of $R^3$, $R^4$, $R^5$, $R^6$ and $R^7$ is —$SO_2NR_2$, where the two R groups are taken together with the nitrogen to which they are attached to form a heterocyclic or substituted heterocyclic ring. In one such variation, $R^3$ is —$SO_2NR_2$, where the two R groups are taken together with the nitrogen to which they are attached to form a heterocyclic or substituted heterocyclic ring. In another variation, $R^3$ is —$SO_2NR_2$, where the two R groups are taken together with the nitrogen to which they are attached to form a heterocyclic or substituted heterocyclic ring and $R^4$, $R^5$, $R^6$ and $R^7$ are H. In a particular variation, $R^3$ is —$SO_2NR_2$, where the two R groups are taken together with the nitrogen to which they are attached to form a heterocyclic or substituted heterocyclic ring and $R^4$, $R^5$, $R^6$ and $R^7$ are H and $R^1$ and $R^2$ are H. In one variation, at least one of $R^3$, $R^4$, $R^5$, $R^6$ and $R^7$ is —$SO_2NR_2$, where the two R groups are taken together with the nitrogen to which they are attached to form a heterocyclic ring, such as a morpholino ring.

Representative compounds of the formula (I) include, but are not limited to, the compounds listed in Table 1.

TABLE 1

Representative Compounds of Formula (I):

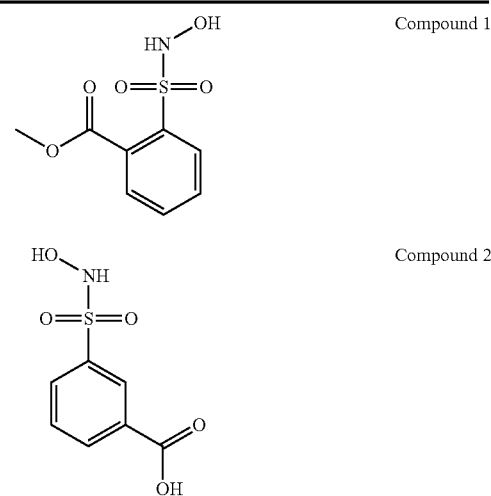

Compound 1

Compound 2

TABLE 1-continued

Representative Compounds of Formula (I):

Compound 3: 4-chloro-3-(N-hydroxysulfamoyl)benzoic acid

Compound 4: 4-bromo-3-(N-hydroxysulfamoyl)benzoic acid

Compound 5: 4-bromo-3-(N-hydroxysulfamoyl)-(morpholin-4-yl)methanone derivative

Compound 6: 4-bromo-N,N-dimethyl-3-(N-hydroxysulfamoyl)benzamide

Compound 7: 4-chloro-N,N-dimethyl-3-(N-hydroxysulfamoyl)benzamide

Compound 8: 2-(morpholinosulfonyl)-N-hydroxybenzenesulfonamide

Compound 9: 2-morpholinoethyl 4-chloro-3-(N-hydroxysulfamoyl)benzoate

Compound 10: 4-chloro-N,N-diethyl-3-(N-hydroxysulfamoyl)benzamide

Compound 11: (4-chloro-3-(N-hydroxysulfamoyl)phenyl)(piperidin-1-yl)methanone

Compound 12: (4-chloro-3-(N-hydroxysulfamoyl)phenyl)(4-fluoropiperidin-1-yl)methanone Compound 13: (4-chloro-3-(N-hydroxysulfamoyl)phenyl)(4,4-difluoropiperidin-1-yl)methanone Compound 14: (4-amino piperidin-1-yl)(4-chloro-3-(N-hydroxysulfamoyl)phenyl)methanone TABLE 1-continued
Representative Compounds of Formula (I):
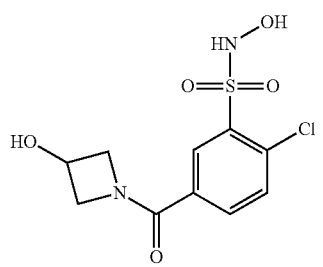 [SMILES: O=C(c1ccc(Cl)c(S(=O)(=O)NO)c1)N1CC(O)C1]
Compound 15
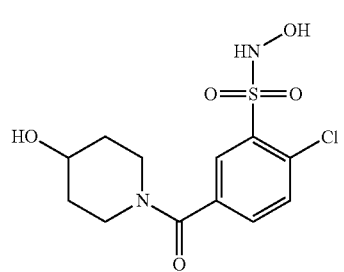 [SMILES: O=C(c1ccc(Cl)c(S(=O)(=O)NO)c1)N1CCC(O)CC1]
Compound 16
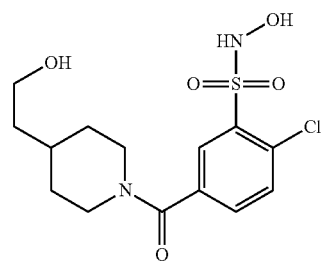 [SMILES: O=C(c1ccc(Cl)c(S(=O)(=O)NO)c1)N1CCC(CCO)CC1]
Compound 17
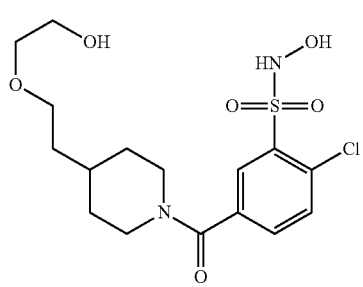 [SMILES: O=C(c1ccc(Cl)c(S(=O)(=O)NO)c1)N1CCC(CCOCCO)CC1]
Compound 18
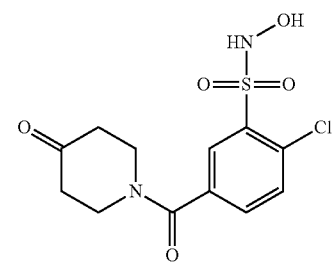 [SMILES: O=C1CCN(C(=O)c2ccc(Cl)c(S(=O)(=O)NO)c2)CC1]
Compound 19
TABLE 1-continued
Representative Compounds of Formula (I):
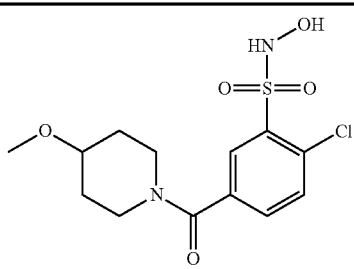
Compound 20
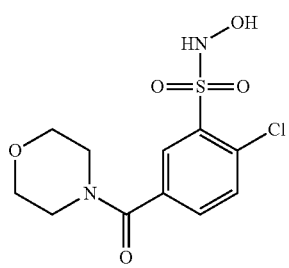 [SMILES: O=C(c1ccc(Cl)c(S(=O)(=O)NO)c1)N1CCOCC1]
Compound 21
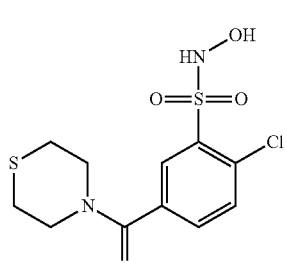
Compound 22
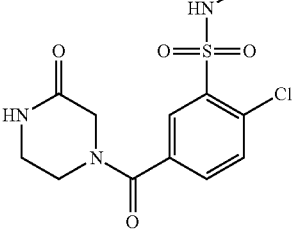
Compound 23
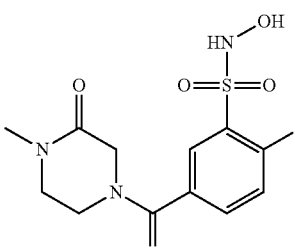
Compound 24
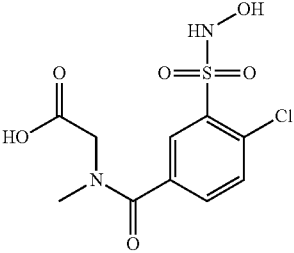 [SMILES: CN(CC(=O)O)C(=O)c1ccc(Cl)c(S(=O)(=O)NO)c1]
Compound 25

TABLE 1-continued
Representative Compounds of Formula (I):
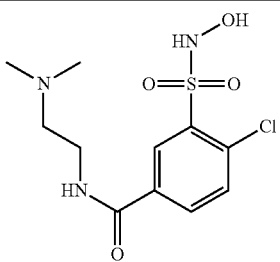 Compound 26
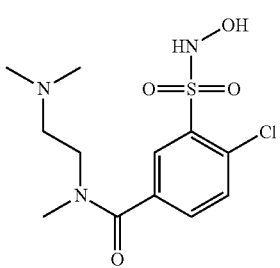 [SMILES: CN(C)CCN(C)C(=O)c1ccc(Cl)c(S(=O)(=O)NO)c1] Compound 27
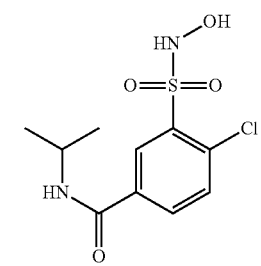 [SMILES: CC(C)NC(=O)c1ccc(Cl)c(S(=O)(=O)NO)c1] Compound 28
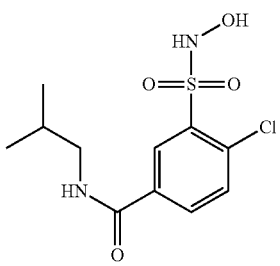 [SMILES: CC(C)CNC(=O)c1ccc(Cl)c(S(=O)(=O)NO)c1] Compound 29
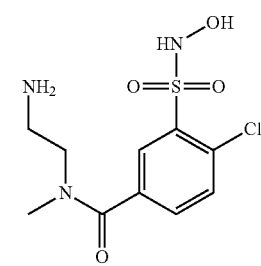 [SMILES: CN(CCN)C(=O)c1ccc(Cl)c(S(=O)(=O)NO)c1] Compound 30
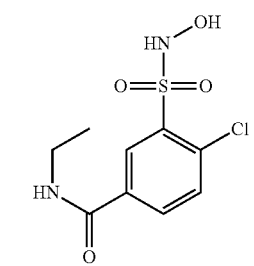 [SMILES: CCNC(=O)c1ccc(Cl)c(S(=O)(=O)NO)c1] Compound 31
TABLE 1-continued
Representative Compounds of Formula (I):
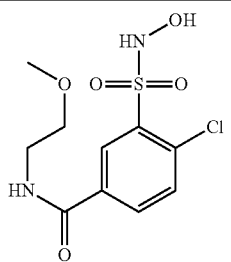 Compound 32
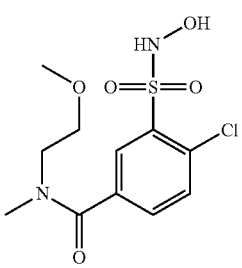 [SMILES: COCCN(C)C(=O)c1ccc(Cl)c(S(=O)(=O)NO)c1] Compound 33
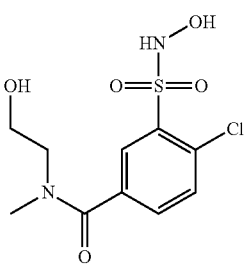 [SMILES: CN(CCO)C(=O)c1ccc(Cl)c(S(=O)(=O)NO)c1] Compound 34
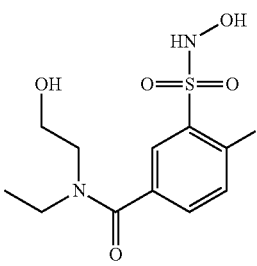 Compound 35
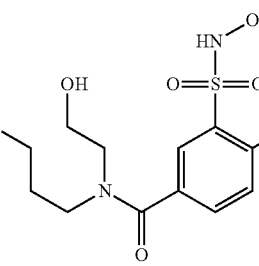 Compound 36
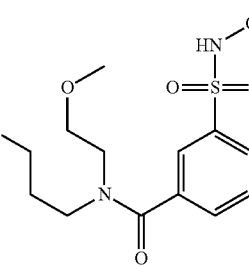 Compound 37

TABLE 1-continued
Representative Compounds of Formula (I):
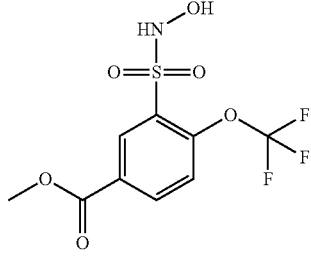 [SMILES: COC(=O)c1ccc(OC(F)(F)F)c(S(=O)(=O)NO)c1]
Compound 38
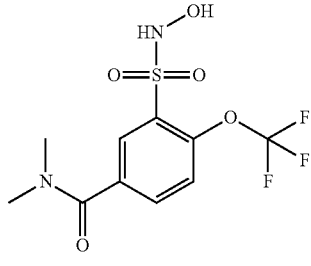 [SMILES: CN(C)C(=O)c1ccc(OC(F)(F)F)c(S(=O)(=O)NO)c1]
Compound 39
Compound 40
Compound 41
Compound 42
Compound 43
TABLE 1-continued
Representative Compounds of Formula (I):
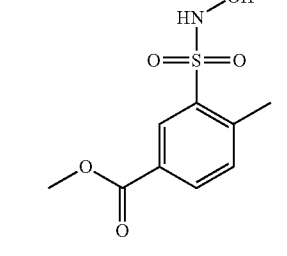
Compound 44
Compound 45
Compound 46
Compound 47
Compound 48
Compound 49

TABLE 1-continued

Representative Compounds of Formula (I):

Compound 50, 51, 52, 53, 54, 55, 56, 57, 58, 59, 60, 61

TABLE 1-continued
Representative Compounds of Formula (I):
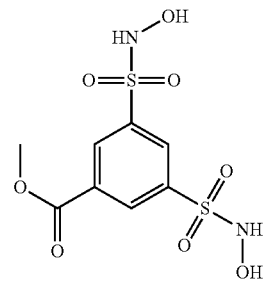 [SMILES: COC(=O)c1cc(S(=O)(=O)NO)cc(S(=O)(=O)NO)c1]
Compound 62
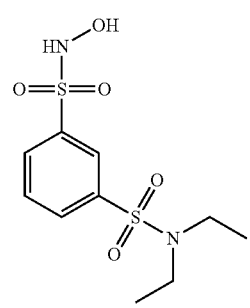 [SMILES: CCN(CC)S(=O)(=O)c1cccc(S(=O)(=O)NO)c1]
Compound 63
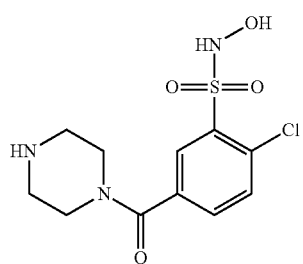 [SMILES: O=C(c1ccc(Cl)c(S(=O)(=O)NO)c1)N1CCNCC1]
Compound 64
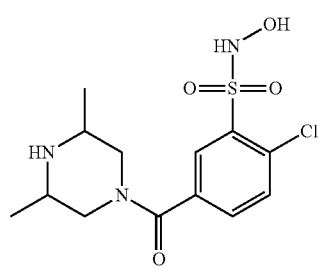 [SMILES: CC1CN(C(=O)c2ccc(Cl)c(S(=O)(=O)NO)c2)CC(C)N1]
Compound 65
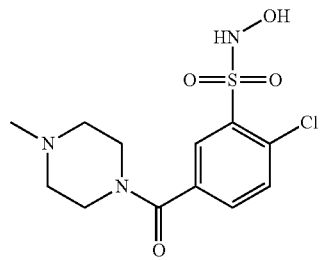 [SMILES: CN1CCN(C(=O)c2ccc(Cl)c(S(=O)(=O)NO)c2)CC1]
Compound 66
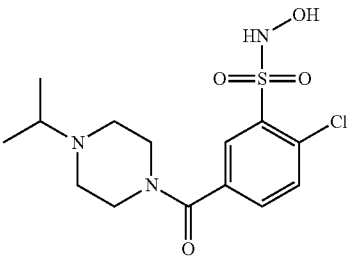 [SMILES: CC(C)N1CCN(C(=O)c2ccc(Cl)c(S(=O)(=O)NO)c2)CC1]
Compound 67
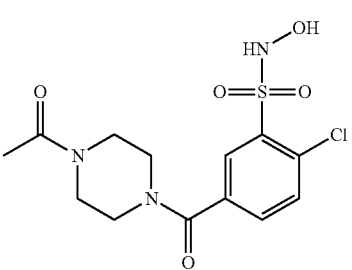 [SMILES: CC(=O)N1CCN(C(=O)c2ccc(Cl)c(S(=O)(=O)NO)c2)CC1]
Compound 68
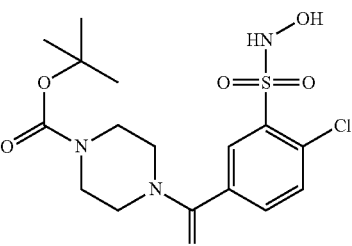
Compound 69
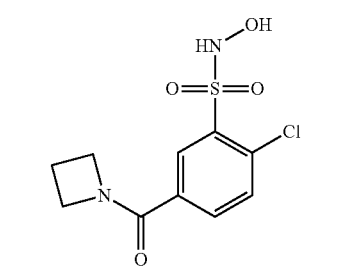 [SMILES: O=C(c1ccc(Cl)c(S(=O)(=O)NO)c1)N1CCC1]
Compound 70
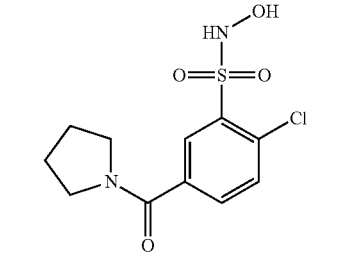 [SMILES: O=C(c1ccc(Cl)c(S(=O)(=O)NO)c1)N1CCCC1]
Compound 71
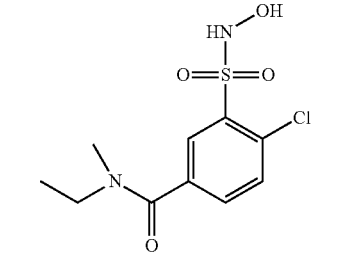 [SMILES: CCN(C)C(=O)c1ccc(Cl)c(S(=O)(=O)NO)c1]
Compound 72

In one embodiment, the nitroxyl donating compound is a compound of the formula (IIa):

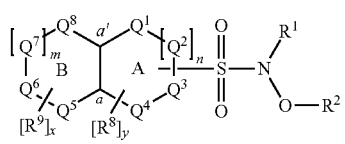

where $R^1$ is H; $R^2$ is H, aralkyl or heterocyclyl; m and n are independently an integer from 0 to 1; x is an integer from 0 to 4 and y is an integer from 0 to 3, provided that at least one of x and y is greater than 0; A is a cycloalkyl, heterocycloalkyl, aromatic or heteroaromatic ring containing ring moieties $Q^1$, $Q^2$, $Q^3$ and $Q^4$, which are taken together with the carbons at positions a and a' to form ring A; B is a cycloalkyl, heterocycloalkyl, aromatic or heteroaromatic ring containing ring moieties $Q^5$, $Q^6$, $Q^7$ and $Q^8$, which are taken together with the carbons at positions a and a' to form ring B; $Q^1$, $Q^2$, $Q^3$, $Q^4$, $Q^5$, $Q^6$, $Q^7$ and $Q^8$ are independently selected from the group consisting of C, $CH_2$, CH, N, $NR^{10}$, O and S; each $R^8$ and $R^9$ is independently selected from the group consisting of halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, $NH_2$, OH, C(O)OH, C(O)Oalkyl, NHC(O)alkylC(O)OH, C(O)$NH_2$, NHC(O)alkylC(O)alkyl, NHC(O)alkenylC(O)OH, NHC(O)$NH_2$, OalkylC(O)Oalkyl, NHC(O)alkyl, C(=N—OH)$NH_2$, cycloalkoxy, cycloalkylsulfanyl, arylsulfanyl, arylsulfinyl, carbonylamino and sulfonylamino, provided that at least one $R^8$ is carbonylamino or sulfonylamino; and, $R^{10}$ is H, alkyl, acyl, or sulfonyl.

In one variation, the compound is of the formula (II) or (IIa) where each $R^8$ and $R^9$ is independently selected from the group consisting of Cl, F, I, Br, $SO_2CH_3$, $SO_2NHOH$, $CF_3$, $CH_3$, $NO_2$, phenyl, CN, $OCH_3$, $OCF_3$, t-Bu, O-iPr, 4-nitrophenyloxy (OPh4-$NO_2$), propane-2-thiyl (SCH($CH_3$)$_2$), propane-2-sulfinyl (S(O)CH($CH_3$)$_2$), morpholino, N-methylpiperazino, dimethylamino, piperidino, cyclohexyloxy, cyclopentylsulfanyl, phenylsulfanyl, phenylsulfinyl, carbonylamino and sulfonylamino, provided that at least one $R^8$ is carbonylamino or sulfonylamino; and $R^{10}$ is H, alkyl, acyl or sulfonyl, provided that when rings A and B form naphthalene, x is an integer from 1 to 3 or y is an integer from 2 to 4.

For any of the variations described for formula (II) or (IIa), included are variations of formula (II) or (IIa) where $R^1$ is H and $R^2$ is H, benzyl or tetrahydropyran-2-yl. In one variation, A and B form a benzofuran or benzothiophene or benzoimidazole or N-alkylbenzoimidazole (such as N-methylbenzoimidazole) or N-acylbenzoimidazole (such as N—C(O)$CH_3$benzoimidazole) or benzothiazole or benzooxazole. In one variation, A and B are other than napthyl or quinoline. In one variation, A and B are napthyl or quinoline. In one variation, A and B form a benzofuran. In one variation, A and B form a benzofuran. In one variation, A and B form a benzothiophene. In one variation, A and B form a benzothiophene, y is 0 and x is 1. In one variation, A and B form naphthyl and x is 0, y is 1. In one variation, ring A is phenyl and ring B is a heteroaryl group, such as when rings A and B form quinoline and ring B is the nitrogen containing ring. The invention also embraces compounds according to any of the variations for formula (II) or (IIa) where y is 0, x is 1 and $R^9$ is a halo, alkyl or perhaloalkyl group. The invention also embraces compounds according to any of the variations for formula (II) or (IIa) where x is 2 and y is 0.

For any of the variations described for formula (II) or (IIa), included are variations of formula (II) or (IIa) where at least one of $R^8$ and $R^9$ is —CONH-alkyl. For any of the variations described for formula (II) or (IIa), included are variations of formula (II) or (IIa) where at least one of $R^8$ and $R^9$ is —CONR-alkyl where R is alkyl. For any of the variations described for formula (II) or (IIa), included are variations of formula (II) or (IIa) where at least one of $R^8$ and $R^9$ is —CONR$_2$ where each R is independently alkyl. In a particular variation of formula (II) or (IIa), y is 0, x is 1 and $R^9$ is —CONR$_2$ where each R is independently alkyl. In another variation of formula (II) or (IIa), y is 0, x is 1 and $R^9$ is —CONR$_2$ where each R is independently lower alkyl, where each lower alkyl can be the same (e.g., —CON(Me)$_2$) or different. For any of the variations described for formula (II) or (IIa), included are variations of formula (II) or (IIa) where at least one of $R^8$ and $R^9$ is —CONR$_2$ where each R taken together with the nitrogen to which it is attached to form a heterocylic or substituted heterocyclic ring. For any of the variations described for formula (II) or (IIa), included are variations of formula (II) or (IIa) where at least one of $R^8$ and $R^9$ is —CONR$_2$ where each R is independently alkyl. For any of the variations described for formula (II) or (IIa), included are variations of formula (II) or (IIa) where at least one of $R^8$ and $R^9$ is —NR$^a$SO$_2$NR-alkyl where $R^a$ and R are independently hydrogen or alkyl. For any of the variations described for formula (II) or (IIa), included are variations of formula (II) or (IIa) where at least one of $R^8$ and $R^9$ is —SO$_2$NH$_2$. For any of the variations described for formula (II) or (IIa), included are variations of formula (II) or (IIa) where at least one of $R^8$ and $R^9$ is —SO$_2$NH$_2$. For any of the variations described for formula (II) or (IIa), included are variations of formula (II) or (IIa) where at least one of $R^8$ and $R^9$ is —SO$_2$NR-alkyl, where R is hydrogen or alkyl. For any of the variations described for formula (II) or (IIa), included are variations of formula (II) or (IIa) where at least one of $R^8$ and $R^9$ is —SO$_2$NR$_2$, where the two R groups are taken together and with the nitrogen atom to which they are attached to form a heterocyclic or substituted heterocyclic ring. In a particular variation of formula (II) or (IIa), y is 0, x is 1 and $R^9$ is —SO$_2$NR$_2$, where the two R groups are taken together and with the nitrogen atom to which they are attached to form a heterocyclic ring. In another variation of formula (II) or (IIa), y is 0, x is 1 and $R^9$ is —SO$_2$NR$_2$, where the two R groups are taken together and with the nitrogen atom to which they are attached to form a morpholino group.

Representative compounds of the formula (IIa) include, but are not limited to, the compounds listed in Table 2.

TABLE 2

Representative Compounds of Formula (IIa):

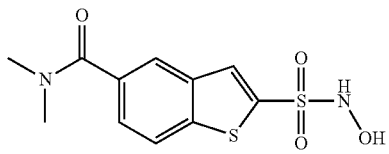 [SMILES: CN(C)C(=O)c1ccc2sc(S(=O)(=O)NO)cc2c1]

Compound 73

TABLE 2-continued

Representative Compounds of Formula (IIa):

Compound 74

Compound 75

Compound 76

In another embodiment, the nitroxyl donating compound is a compound of the formula (III):

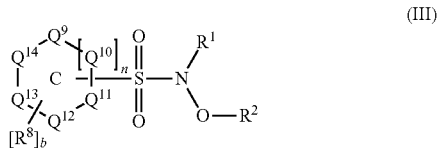

(III)

where $R^1$ is H; $R^2$ is H, aralkyl or heterocyclyl; n is an integer from 0 to 1; b is an integer from 1 to 4; C is a heteroaromatic ring containing ring moieties $Q^9$, $Q^{10}$, $Q^{11}$, $Q^{12}$, $Q^{13}$ and $Q^{14}$ that are independently selected from the group consisting of C, $CH_2$, CH, N, $NR^{10}$, O and S, provided that at least one of $Q^9$, $Q^{10}$, $Q^{11}$, $Q^{12}$, $Q^{13}$ and $Q^{14}$ is N, $NR^{10}$, O or S; each $R^8$ is independently selected from the group consisting of halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, heterocycloalkyl, substituted heterocycloalkyl, dialkylamino, $NH_2$, OH, C(O)OH, C(O)Oalkyl, NHC(O)alkylC(O)OH, C(O)$NH_2$, NHC(O)alkylC(O)alkyl, NHC(O)alkenylC(O)OH, NHC(O)$NH_2$, OalkylC(O)Oalkyl, NHC(O)alkyl, C(=N—OH)$NH_2$, cycloalkoxy, cycloalkylsulfanyl, arylsulfanyl, arylsulfinyl, carbonylamino or sulfonylamino, provided that at least one $R^8$ is carbonylamino or sulfonylamino; and $R^{10}$ is H, alkyl, acyl or sulfonyl.

In one variation, the compound is of the formula (III) and each $R^8$ is independently selected from the group consisting of Cl, F, I, Br, $SO_2CH_3$, $SO_2NHOH$, $CF_3$, $CH_3$, $NO_2$, phenyl, CN, $OCH_3$, $OCF_3$, t-Bu, O-iPr, 4-nitrophenyloxy (OPh4-$NO_2$), propane-2-thiyl (SCH($CH_3$)$_2$), propane-2-sulfinyl (S(O)CH($CH_3$)$_2$), morpholino, N-methyl-piperazino, dimethylamino, piperidino, cyclohexyloxy, cyclopentylsulfanyl, phenylsulfanyl, phenylsulfinyl, carbonylamino or sulfonylamino, provided that at least one $R^8$ is carbonylamino or sulfonylamino. In another variation, the compound is of the formula (III) and each $R^8$ is independently selected from the group consisting of F, Br, Cl, $CF_3$, phenyl, methyl, $SO_2NHOH$, morpholino, piperidino, 4-methyl-piperazino, carbonylamino and sulfonylamino, provided that at least one $R^8$ is carbonylamino or sulfonylamino.

For any of the variations described for formula (III), included are variations of formula (III) where $R^1$ is H and $R^2$ is H, benzyl or tetrahydropyran-2-yl. In one variation, n is 0 and C is a thiophene or isoxazole or pyrazole or pyrrole or imidazole or furan or thiazole or triazole or N-methylimidazole or thiadiazole. In one variation, C is other than thienyl. In another variation, n is 0 and C is a thiophene or isoxazole or pyrazole or pyrrole or imidazole or furan or thiazole or triazole or N-methylimidazole or thiadiazole. In one variation, n is 1 and C is a pyrimidine or pyrazine or pyridine. In one variation, n is 1 and C is a pyrimidine or pyrazine or pyridine and b is 1. In one variation, n is 1 and C is a pyrimidine or pyrazine or pyridine, b is 1, and at least one $R^8$ is chloro or morpholino or piperidino or N-methylpiperizino. In one variation, C is thiophene and b is 1. In one variation, C is thiophene, b is 1 and at least one $R^8$ is halo. In one variation, C is thiophene.

For any of the variations described for formula (III), included are variations of formula (III) where at least one $R^8$ is —$CONH_2$. In one variation, C is a thiophene substituted with —$CONH_2$, and optionally substituted with an additional $R^8$, such as an amino group. For any of the variations described for formula (III), included are variations of formula (III) where at least one $R^8$ is —CONH-alkyl. For example, compounds wherein $R^8$ is —CONH-lower alkyl (e.g., isopropyl) are encompassed. For any of the variations described for formula (III), included are variations of formula (III) where at least one $R^8$ is —CONH-substituted alkyl. In a particular variation, C is thiophene, $R^1$ and $R^2$ are both H and at least one $R^8$ is —CONH-substituted alkyl. For any of the variations described for formula (III), included are variations of formula (III) where at least one $R^8$ is —CONR-alkyl where R is alkyl. For any of the variations described for formula (III), included are variations of formula (III) where at least one $R^8$ is —$CONR_2$ where each R is independently alkyl, such as —CON(Me)$_2$. In a particular variation, C is a thiophene, b is 2, one of $R^8$ is —$CONR_2$ where each R is independently alkyl (such as —CON(Me)$_2$) and the other $R^8$ is —S(O)$_2$Alkyl, aryl, heteroaryl, or —S-alkyl. For any of the variations described for formula (III), included are variations of formula (III) where at least one $R^8$ is —$CONR_2$ where each R is independently a substituted alkyl, such as —$CH_2CH_2OCH_3$. For any of the variations described for formula (III), included are variations of formula (III) where at least one $R^8$ is —$CONR_2$ where each R taken together with the nitrogen to which it is attached to form a heterocyclic or substituted heterocyclic ring. In a particular variation, C is thiophene, $R^1$ and $R^2$ are both H and at least one $R^8$ is —$CONR_2$ where each R taken together with the nitrogen to which it is attached to form a heterocyclic or substituted heterocyclic ring, such as morpholino. In a another variation, C is thiophene, $R^1$ and $R^2$ are both H, b is 1 or 2, at least one $R^8$ is —$CONR_2$ where each R taken together with the nitrogen to which it is attached to form a heterocyclic ring selected from piperidinyl and morpholinyl and when b is 2, the $R^8$ that is other than is —$CONR_2$ is selected from halo, nitro and —$OR^{11}$, such as —Oalkyl (e.g., methoxy). In a another variation, C is thiophene, $R^1$ and $R^2$ are both H, b is 1 or 2, at least one $R^8$ is —$CONR_2$ where each R taken together with the nitrogen to which it is attached to form a heterocyclic ring substituted with 1 or 2 moieties selected from lower alkyl, carboxylester, acyl, halo, amino, hydroxyl, substituted lower alkyl, oxo and alkoxy. For example, in any variation herein where $R^8$ is —$CONR_2$ where each R taken together with the nitrogen to which it is attached to form a substituted heterocyclic ring selected from 1-methyl-piperaz-4-yl, 4-fluoropiperidyl and 4-hydroxypiperidyl. For any variation, e.g., when C is thiophene substituted with $R^8$ is —$CONR_2$, C may also be substituted with a moiety selected from halo, amino, hydroxyl, alkoxy, nitro and cyano. For any of the variations described for formula (III), included are variations of formula (III) where at least one $R^8$ is —$CONR_2$ where each R is independently alkyl. For any of the variations described for formula (III), included are variations of formula (III) where at least one $R^8$ is —$NR^aSO_2NR$-alkyl where $R^a$ and R are independently hydrogen or alkyl. For any of the variations described for formula (III), included are variations of formula (III) where at least one $R^8$ is —$SO_2NH_2$. For any of the variations described for formula (III), included are variations of formula (III) where at least one $R^8$ is —$SO_2NH_2$. For any of the variations described for formula (III), included are variations of formula (III) where at least one $R^8$ is —$SO_2NR$-alkyl, where R is hydrogen or alkyl. For any of the variations described for formula (III), included are variations of formula (III) where at least one $R^8$ is —$SO_2NR_2$, where the two R groups are taken together and with the nitrogen atom to which they are attached to form a heterocyclic or substituted heterocyclic ring.

Representative compounds of the formula (III) include, but are not limited to, the compounds listed in Table 3.

TABLE 3

Representative Compounds of Formula (III):

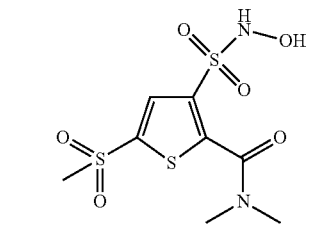 [SMILES: CN(C)C(=O)c1sc(S(C)(=O)=O)cc1S(=O)(=O)NO]

Compound 77

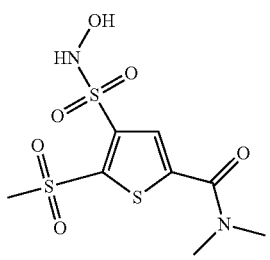

Compound 78

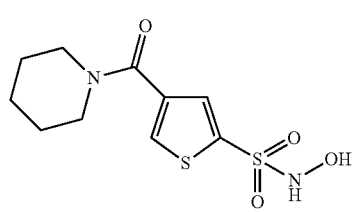 [SMILES: O=C(c1csc(S(=O)(=O)NO)c1)N1CCCCC1]

Compound 79

TABLE 3-continued

Representative Compounds of Formula (III):

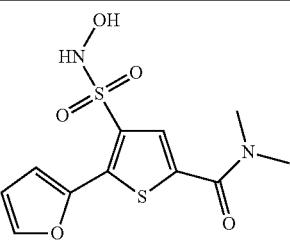

Compound 80

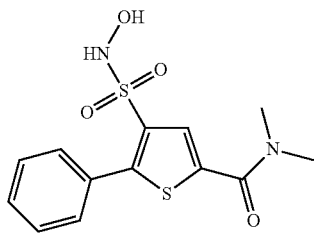 [SMILES: CN(C)C(=O)c1cc(S(=O)(=O)NO)c(-c2ccccc2)s1]

Compound 81

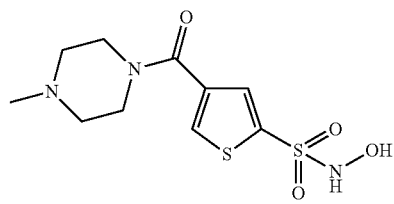 [SMILES: CN1CCN(C(=O)c2csc(S(=O)(=O)NO)c2)CC1]

Compound 82

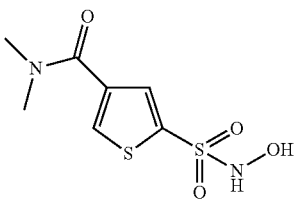

Compound 83

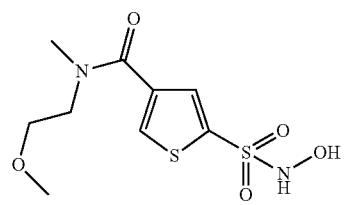 [SMILES: COCCN(C)C(=O)c1csc(S(=O)(=O)NO)c1]

Compound 84

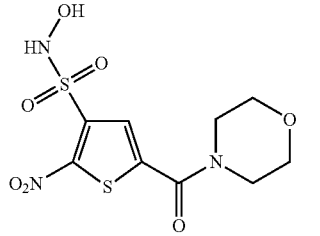 [SMILES: O=C(c1cc(S(=O)(=O)NO)c([N+](=O)[O-])s1)N1CCOCC1]

Compound 85

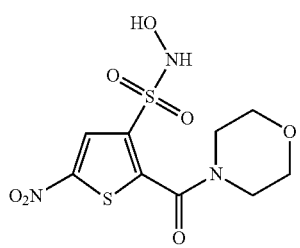 [SMILES: O=C(c1sc([N+](=O)[O-])cc1S(=O)(=O)NO)N1CCOCC1]

Compound 86

TABLE 3-continued

Representative Compounds of Formula (III):

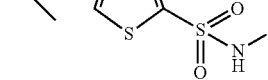
Compound 87

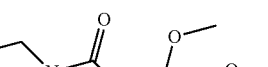
Compound 88

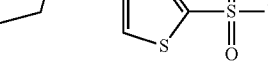
Compound 89

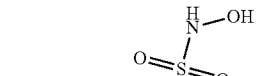
Compound 90

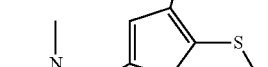
Compound 91

Compound 92

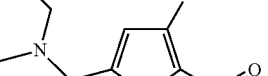
Compound 93

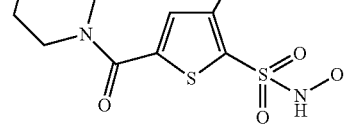
Compound 94

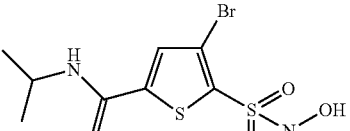
Compound 95

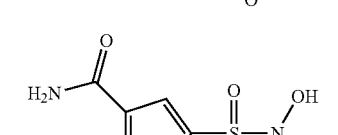
Compound 96

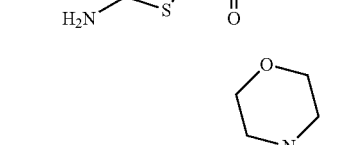
Compound 97

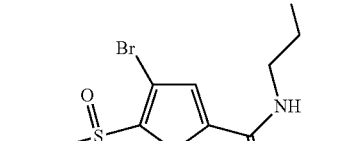
Compound 98

Compounds for Use in the Methods

The methods described employ compounds of the invention that donate an effective amount of nitroxyl under physiological conditions. Any of the methods may employ an N-hydroxylsulfonamide compound described above under "N-Hydroxysulfonamide Compounds."

For any of the compounds of the invention, such as the compounds of formula (I), (II) or (III) or other compounds for use in the methods described herein, recitation or depiction of the parent compound intends and includes all salts, solvates, hydrates, polymorphs, or prodrugs thereof, where applicable. As such, all salts, such as pharmaceutically acceptable salts, solvates, hydrates, polymorphs and prodrugs of a compound are embraced by the invention and described herein the same as if each and every salts, solvate, hydrate, polymorph, or prodrug were specifically and individually listed.

For all compounds disclosed herein, where applicable due to the presence of a stereocenter, the compound is intended to embrace all possible stereoisomers of the compound depicted or described. Compositions comprising a compound with at least one stereocenter are also embraced by the invention, and includes racemic mixtures or mixtures containing an enantiomeric excess of one enantiomer or single diastereomers or diastereomeric mixtures. All such isomeric forms of these compounds are expressly included herein the same as if each and every isomeric form were specifically and individually listed. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are also expressly included in the present invention. The compounds herein may also be represented in multiple tautomeric forms, in such instances, the invention expressly includes all tautomeric forms of the compounds described herein, even though only a single tautomeric form may be represented. Also embraced are compositions of substantially pure compound. A composition of substantially pure compound means that the composition contains no more than 25%, or no more than 15%, or no more than 10%, or no more than 5%, or no more than 3% impurity, or no more than 1% impurity, such as a different biologically active compound, which may include a different stereochemical form of the compound if the composition contains a substantially pure single isomer.

The compounds of the invention can be made according to the general methods described in Schemes A-D or by procedures known in the art. Starting materials for the reactions are either commercially available or may be prepare by known procedures or obvious modifications thereof. For example, many of the starting materials are available from commercial suppliers such as Sigma-Aldrich. Others may be prepared by procedures or obvious modifications thereof described in standard reference texts such as March's Advanced Organic Chemistry, (John Wiley and Sons) and Larock's Comprehensive Organic Transformations (VCH Publishers Inc.).

Scheme A. General Synthesis of N-Hydroxysulfonamides (Method 1).

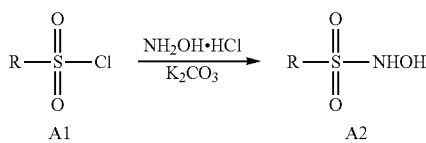

In Scheme A, a solution of hydroxylamine hydrochloride in water is chilled to 0° C. A solution of potassium carbonate in water is added dropwise, maintaining an internal reaction temperature between about 5° C. and about 15° C. The reaction mixture is stirred for about 15 minutes, whereupon tetrahydrofuran (THF) and methanol (MeOH) are added. Compound A1 (where R is an alkyl, aryl or heterocyclyl group) is added portionwise maintaining a temperature below about 15° C. and the reaction mixture is stirred at ambient temperature until complete consumption of the sulfonyl chloride is observed by thin layer chromatography (TLC). The resulting suspension is concentrated to remove any volatiles and the aqueous suspension is extracted with diethyl ether. The organic portion is dried over magnesium sulfate, filtered and concentrated in vacuo to yield the crude N-hydroxy sulphonamide A2. Purification may be achieved by conventional methods, such as chromatography, filtration, crystallization and the like.

Scheme B. General Synthesis of N-Hydroxysulfonamides (Method 2).

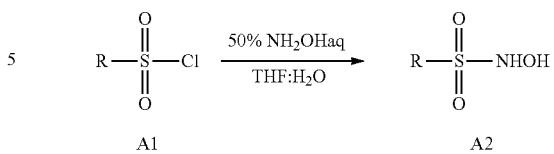

In Scheme B, a solution of aqueous hydroxylamine in water and THF is chilled to −5° C. Compound A1 (where R is an alkyl, aryl or heterocyclyl group) is added portionwise maintaining a temperature below about 10° C. and the reaction mixture is stirred at ambient temperature until complete consumption of the sulfonyl chloride is observed by thin layer chromatography (TLC). The resulting suspension is concentrated to remove any volatiles and the aqueous suspension is extracted with diethyl ether. The organic portion is dried over magnesium sulfate, filtered and concentrated in vacuo to yield the crude N-hydroxy sulphonamide A2. Purification may be achieved by conventional methods, such as chromatography, filtration, crystallization and the like.

Scheme C. General Synthesis of Intermediate N-Benzyloxysulfonamides.

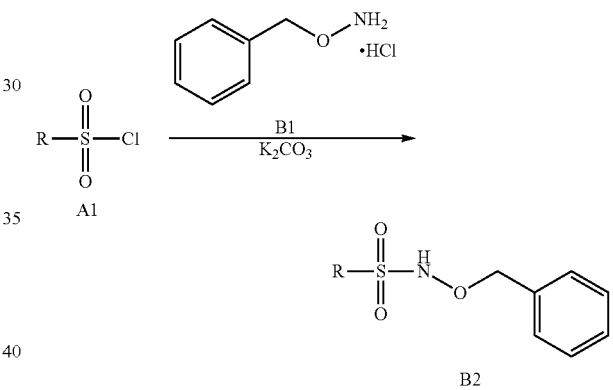

N-Benzyloxysulfonamides are chemical intermediates that are used as protected N-hydroxysulfonamides for the further modification of the R moiety of compound B2. In Scheme B, a suspension of O-benzylhydroxylamine hydrochloride B1 in methanol and water is added to a chilled solution of potassium carbonate in water, maintaining an internal reaction temperature below about 10° C. The reaction mixture is stirred for about 5 minutes, whereupon THF and A1 (where R is an alkyl, aryl or heterocyclyl group) are added. The reaction mixture is stirred at ambient temperature until complete consumption of the sulfonyl chloride was observed by TLC. The resulting suspension is concentrated in vacuo to remove any volatiles, and the aqueous suspension was extracted with diethyl ether. The organic layer was dried over sodium sulfate, filtered and concentrated in vacuo to yield the crude target compound B2. Purification may be achieved by conventional methods, such as chromatography, filtration, crystallization and the like. The reaction product B2 may be deprotected by removing the benzyl group. For instance, a suspension of 10% palladium on charcoal may be added to a suspension of B2 in methanol. The reaction mixture is stirred under a hydrogen atmosphere at ambient temperature and atmospheric pressure overnight. The reaction mixture is filtered through microfibre glass paper. The resulting filtrate is concentrated in vacuo, and the residue purified by conventional methods to yield the corresponding N-hydroxylsulfonamide.

Scheme D. General Synthesis of Intermediate N-(tetrahydro-pyran-2-yloxy)sulfonamides.

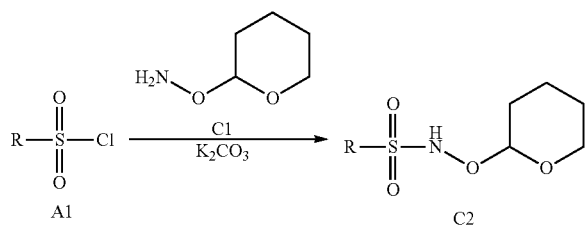

N-(tetrahydro-pyran-2-yloxy)sulfonamides are chemical intermediates that are used as protected N-hydroxysulfonamides for the further modification of the R moiety of compound C2. In Scheme C, to a solution of C1 in water at 0° C. is added a solution of potassium carbonate in water dropwise, maintaining an internal reaction temperature below about 10° C. After about 15 minutes, methanol and THF are added dropwise, followed by A1 portionwise. The reaction mixture is stirred at ambient temperature until complete consumption of the sulfonyl chloride is observed by TLC. The resulting suspension was concentrated to remove any volatiles and the aqueous suspension was extracted with diethyl ether. The organic portion is dried over sodium sulfate, filtered and concentrated in vacuo to yield the crude target compound C2. Purification may be achieved by conventional methods, such as chromatography, filtration, crystallization and the like. Deprotection of C2 to yield the corresponding N-hydroxylsulfonamide may be carried out according to methods known in the art.

Methods of Using the Compounds and Compositions

The compounds and compositions herein may be used to treat and/or prevent the onset and/or development of a disease or condition that is responsive to nitroxyl therapy.

The invention embraces methods of administering to an individual (including an individual identified as in need of such treatment) an effective amount of a compound to produce a desired effect. Identifying a subject in need of such treatment can be in the judgment of a physician, clinical staff, emergency response personnel or other health care professional and can be subjective (e.g. opinion) or objective (e.g. measurable by a test or diagnostic method).

One embodiment provides a method of modulating (including increasing) in vivo nitroxyl levels in an individual in need thereof, the method comprising administering to the individual a compound that donates nitroxyl under physiological conditions or a pharmaceutically acceptable salt thereof. An individual is in need of nitroxyl modulation if they have or are suspected of having or are at risk of having or developing a disease or condition that is responsive to nitroxyl therapy.

Particular diseases or conditions embraced by the methods of the invention include cardiovascular diseases such as heart failure or conditions and diseases or conditions that implicate or may implicate ischemia/reperfusion injury. These methods are described in more detail below.

Compositions comprising a nitroxyl-donating compound of the invention are embraced by the invention. However, the methods described may use more than one nitroxyl donating compound; for example, the methods may employ Angeli's salt and an N-hydroxysulfonamide of the present invention or two or more N-hydroxysulfonamides of the present invention, which may be administered together or sequentially.

Cardiovascular Diseases

Provided herein are methods of treating cardiovascular diseases such as heart failure by administering an effective amount of at least one nitroxyl donating compound to an individual in need thereof. Also provided are methods of administering a therapeutically effective dose of at least one nitroxyl donating compound in combination with at least one other positive inotropic agent to an individual in need thereof. Further provided are methods of administering a therapeutically effective amount of at least one nitroxyl donating compound to an individual who is receiving beta-antagonist therapy and who is experiencing heart failure. Methods are provided herein for administering compounds of the invention in combination with beta-adrenergic agonists to treat heart failure. Such agonists include dopamine, dobutamine, and isoproterenol, and analogs and derivatives of such compounds. Also provided are methods of administering nitroxyl donors to individuals receiving treatment with beta-antagonizing agents such as propranolol, metoprolol, bisoprolol, bucindolol, and carvedilol. Further, methods are provided herein for treating specific classifications of heart failure, such as Class III heart failure and acute heart failure.

Also embraced by the invention is a method of treating congestive heart failure (CHF), including acute congestive heart failure, by administering an effective amount at least one nitroxyl donating compound to an individual in need thereof, which individual may be experiencing heart failure. Also disclosed is a method of treating CHF by administering an effective amount of at least one nitroxyl donating compound in combination with an effective amount of at least one other positive inotropic agent to an individual in need thereof, which individual may be experiencing heart failure. In one variation, the other positive inotrope is a beta-adrenergic agonist, such as dobutamine. The combined administration of a nitroxyl donor and at least one other positive inotropic agent comprises administering the nitroxyl donor either sequentially with the other positive inotropic agent for example, the treatment with one agent first and then the second agent, or administering both agents at substantially the same time, wherein there is an overlap in performing the administration. With sequential administration, an individual is exposed to the agents at different times, so long as some amount of the first agent, which is sufficient to be therapeutically effective in combination with the second agent, remains in the subject when the other agent is administered. Treatment with both agents at the same time can involve administration of the agents in the same dose, such as a physically mixed dose, or in separate doses administered at the same time.

In particular an embodiment, a nitroxyl donor is administered to an individual experiencing heart failure that is receiving beta-antagonist therapy. A beta-antagonist (also known as a beta-blocker) includes any compound that effectively acts as an antagonist at a subject's beta-adrenergic receptors, and provides desired therapeutic or pharmaceutical results, such as diminished vascular tone and/or heart rate. A subject who is receiving beta-antagonist therapy is any subject to whom a beta-antagonist has been administered, and in whom the beta-antagonist continues to act as an antagonist at the subject's beta-adrenergic receptors. In particular embodiments a determination of whether a subject is receiving beta-blocking therapy is made by examination of the subject's medical history. In other embodiments the subject is screened for the presence of beta-blocking agents by chemical tests, such as high-speed liquid chromatography as described in Thevis et al., *Biomed. Chromatogr.,* 15:393-402 (2001).

The administration of a nitroxyl donating compound either alone, in combination with a positive inotropic agent, or to a subject receiving beta-antagonist therapy, is used to treat heart failure of all classifications. In particular embodiments a nitroxyl donating compound is used to treat early-stage chronic heart failure, such as Class II heart failure. In other embodiments a nitroxyl donating compound is used in combination with a positive inotropic agent, such as isoproterenol to treat Class IV heart failure. In still other embodiments a nitroxyl donating compound is used in combination with another positive inotropic agent, such as isoproterenol to treat acute heart failure. In some embodiments, when a nitroxyl donor is used to treat early stage heart failure, the dose administered is lower than that used to treat acute heart failure. In other embodiments the dose is the same as is used to treat acute heart failure.

Ischemia/Reperfusion Injury

The invention embraces methods of treating or preventing or protecting against ischemia/reperfusion injury. In particular, compounds of the invention are beneficial for individuals at risk for an ischemic event. Thus, provided herein is a method of preventing or reducing the injury associated with ischemia/reperfusion by administering an effective amount of at least one nitroxyl donating compound to an individual, preferably prior to the onset of ischemia. A compound of the invention may be administered to an individual after ischemia but before reperfusion. A compound of the invention may also be administered after ischemia/reperfusion, but where the administration protects against further injury. Also provided is a method in which the individual is demonstrated to be at risk for an ischemic event. Also disclosed is a method of administering a nitroxyl donating compound to an organ that is to be transplanted in an amount effective to reduce ischemia/reperfusion injury to the tissues of the organ upon reperfusion in the recipient of the transplanted organ.

Nitroxyl donors of the invention may thus be used in methods of preventing or reducing injury associated with future ischemia/reperfusion. For example, administration of a nitroxyl donor prior to the onset of ischemia may reduce tissue necrosis (the size of infarct) in at-risk tissues. In live subjects this may be accomplished by administering an effective amount of a nitroxyl donating compound to an individual prior to the onset of ischemia. In organs to be transplanted this is accomplished by contacting the organ with a nitroxyl donor prior to reperfusion of the organ in the transplant recipient. Compositions comprising more than one nitroxyl-donating compound also could be used in the methods described, for example, Angeli's salt and an N-hydroxysulfonamide of the present invention or two or more N-hydroxysulfonamides of the present invention. The nitroxyl-donating compound also can be used in combination with other classes of therapeutic agents that are designed to minimize ischemic injury, such as beta blockers, calcium channel blockers, anti-platelet therapy or other interventions for protecting the myocardium in individuals with coronary artery disease.

One method of administering a nitroxyl donor to live subjects includes administration of the nitroxyl-donating compound prior to the onset of ischemia. This refers only to the onset of each instance of ischemia and would not preclude performance of the method with subjects who have had prior ischemic events, i.e., the method also contemplates administration of nitroxyl-donating compounds to a subject who has had an ischemic event in the past.

Individuals can be selected who are at risk of a first or subsequent ischemic event. Examples include individuals with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia such as a cerebrovascular accident CVA). In particular examples of the methods, individuals are selected for treatment who are at risk of future ischemia, but who have no present evidence of ischemia (such as electrocardiographic changes associated with ischemia (for example, peaked or inverted T-waves or ST segment elevations or depression in an appropriate clinical context), elevated CKMB, or clinical evidence of ischemia such as crushing sub-sternal chest pain or arm pain, shortness of breath and/or diaphoresis). The nitroxyl-donating compound also could be administered prior to procedures in which myocardial ischemia may occur, for example an angioplasty or surgery (such as a coronary artery bypass graft surgery). Also embraced is a method of administering a nitroxyl-donating compound to an individual at demonstrated risk for an ischemic event. The selection of an individual with such a status could be performed by a variety of methods, some of which are noted above. For example, an individual with one of more of an abnormal EKG not associated with active ischemia, prior history of myocardial infarction, elevated serum cholesterol, etc., would be at risk for an ischemic event. Thus, an at-risk individual could be selected by physical testing or eliciting the potential subject's medical history to determine whether the subject has any indications of risk for an ischemic event. If risk is demonstrated based on the indications discussed above, or any other indications that one skilled in the art would appreciate, then the individual would be considered at demonstrated risk for an ischemic event.

Ischemia/reperfusion may damage tissues other than those of the myocardium and the invention embraces methods of treating or preventing such damage. In one variation, the method finds use in reducing injury from ischemia/reperfusion in the tissue of the brain, liver, gut, kidney, bowel, or in any other tissue. The methods preferably involve administration of a nitroxyl donor to an individual at risk for such injury. Selecting a person at risk for non-myocardial ischemia could include a determination of the indicators used to assess risk for myocardial ischemia. However, other factors may indicate a risk for ischemia/reperfusion in other tissues. For example, surgery patients often experience surgery related ischemia. Thus, individuals scheduled for surgery could be considered at risk for an ischemic event. The following risk factors for stroke (or a subset of these risk factors) would demonstrate a subject's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, "Preventing ischemic stroke: current approaches to primary and secondary prevention," *Postgrad. Med.,* 107(6):34-50 (2000). Further, complications of untreated infectious diarrhea in the elderly can include myocardial, renal, cerebrovascular and intestinal ischemia. Slotwiner-Nie & Brandt, "Infectious diarrhea in the elderly," Gastroenterol, *Clin. N. Am.,* 30(3): 625-635 (2001). Alternatively, individuals could be selected based on risk factors for ischemic bowel, kidney or liver disease. For example, treatment would be initiated in elderly subjects at risk of hypotensive episodes (such as surgical blood loss). Thus, subjects presenting with such an indication would be considered at risk for an ischemic event. Also embraced is a method of administering a nitroxyl donating compound of the invention to an individual who has any one or more of the conditions listed herein, such as diabetes mellitus or hypertension. Other conditions that may result in ischemia such as cerebral arteriovenous malformation would be considered to demonstrate risk for an ischemic event.

The method of administering nitroxyl to organs to be transplanted includes administration of nitroxyl prior to removal of the organ from the donor, for example through the perfusion cannulas used in the organ removal process. If the organ donor is a live donor, for example a kidney donor, the nitroxyl donor can be administered to the organ donor as described above for a subject at risk for an ischemic event. In other cases the nitroxyl donor can be administered by storing the organ in a solution comprising the nitroxyl donor. For example, the nitroxyl donor can be included in the organ preservation solution, such as University of Wisconsin "UW" solution, which is a solution comprising hydroxyethyl starch substantially free of ethylene glycol, ethylene chlorohydrin and acetone (see U.S. Pat. No. 4,798,824).

Pharmaceutical Composition, Dosage Forms and Treatment Regimens

Also included are pharmaceutically acceptable compositions comprising a compound of the invention or pharmaceutically acceptable salt thereof and any of the methods may employ the compounds of the invention as a pharmaceutically acceptable composition. A pharmaceutically acceptable composition includes one or more of the compounds of the invention together with a pharmaceutically acceptable carrier. The pharmaceutical compositions of the invention include those suitable for oral, rectal, nasal, topical (including buccal and sublingual), vaginal or parenteral (including subcutaneous, intramuscular, intravenous and intradermal) administration.

The compounds or compositions may be prepared as any available dosage form. Unit dosage forms are also intended, which includes discrete units of the compound or composition such as capsules, sachets or tablets each containing a predetermined amount of the compound; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet containing the compound or composition may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US Patents, some of which include, but are not limited to, U.S. Pat. Nos. 4,369,174 and 4,842,866, and references cited therein. Coatings can be used for delivery of compounds to the intestine (see, e.g., U.S. Pat. Nos. 6,638,534, 5,217,720 and 6,569,457, and references cited therein). A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use.

Extemporaneous injection solutions and suspensions may be prepared from sterile powders, granules and tablets.

Administration of the compounds or compositions to an individual may involve systemic exposure or may be local administration, such as when a compound or composition is to be administered at the site of interest. Various techniques can be used for providing the subject compositions at the site of interest, such as via injection, use of catheters, trocars, projectiles, pluronic gel, stems, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. The methods of the invention embrace administration of the compounds to an organ to be donated (such as to prevent ischemia/reperfusion injury). Accordingly, organs that are removed from one individual for transplant into another individual may be bathed in a medium containing or otherwise exposed to a compound or composition as described herein.

The compounds of the invention, such as those of the formulae herein, may be administered in any suitable dosage amount, which may include dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.1 mg/kg/day and 90 mg/kg/day and the upper end of the range is any amount between 1 mg/kg/day and -32 100 mg/kg/day (e.g., 0.5 mg/kg/day and 2 mg/kg/day, 5 mg/kg/day and 20 mg/kg/day). The dosing interval can be adjusted according to the needs of the individual. For longer intervals of administration, extended release or depot formulations can be used. The dosing can be commensurate with intravenous administration. For instance, the compound can be administered, such as in a pharmaceutical composition that is amenable to intravenous administration, in an amount of between about 0.01

μg/kg/min to about 100 μg/kg/min or between about 0.05 μg/kg/min to about 95 μg/kg/min or between about 0.1 μg/kg/min to about 90 μg/kg/min or between about 1.0 μg/kg/min to about 80 μg/kg/min or between about 10.0 μg/kg/min to about 70 μg/kg/min or between about 20 μg/kg/min to about 60 μg/kg/min or between about 30 μg/kg/min to about 50 μg/kg/min or between about 0.01 μg/kg/min to about 1.0 μg/kg/min or between about 0.01 μg/kg/min to about 10 μg/kg/min or between about 0.1 μg/kg/min to about 1.0 μg/kg/min or between about 0.1 μg/kg/min to about 10 μg/kg/min or between about 1.0 μg/kg/min to about 5 μg/kg/min or between about 70 μg/kg/min to about 100 μg/kg/min or between about 80 μg/kg/min to about 90 μg/kg/min. In one variation, the compound is administered to an individual, such as in a pharmaceutical composition that is amenable to intravenous administration, in an amount of at least about 0.01 μg/kg/min or at least about 0.05 μg/kg/min or at least about 0.1 μg/kg/min or at least about 0.15 μg/kg/min or at least about 0.25 μg/kg/min or at least about 0.5 μg/kg/min or at least about 1.0 μg/kg/min or at least about 1.5 μg/kg/min or at least about 5.0 μg/kg/min or at least about 10.0 μg/kg/min or at least about 20.0 μg/kg/min or at least about 30.0 μg/kg/min or at least about 40.0 μg/kg/min or at least about 50.0 μg/kg/min or at least about 60.0 μg/kg/min or at least about 70.0 μg/kg/min or at least about 80.0 μg/kg/min or at least about 90.0 μg/kg/min or at least about 100.0 μg/kg/min or more. In another variation, the compound is administered to an individual, such as in a pharmaceutical composition that is amenable to intravenous administration, in an amount of less than about 100.0 μg/kg/min or less than about 90.0 μg/kg/min or less than about 80.0 μg/kg/min or less than about 80.0 μg/kg/min or less than about 70.0 μg/kg/min or less than about 60.0 μg/kg/min or less than about 50.0 μg/kg/min or less than about 40.0 μg/kg/min or less than about 30.0 μg/kg/min or less than about 20.0 μg/kg/min or less than about 10.0 μg/kg/min or less than about 5.0 μg/kg/min or less than about 2.5 μg/kg/min or less than about 1.0 μg/kg/min or less than about 0.5 μg/kg/min or less than about 0.05 μg/kg/min or less than about 0.15 μg/kg/min or less than about 0.1 μg/kg/min or less than about 0.05 μg/kg/min or less than about 0.01 μg/kg/min.

The invention further provides kits comprising one or more compounds as described herein. The kits may employ any of the compounds disclosed herein and instructions for use. The compound may be formulated in any acceptable form. The kits may be used for any one or more of the uses described herein, and, accordingly, may contain instructions for any one or more of the stated uses (e.g., treating and/or preventing and/or delaying the onset and/or the development of heart failure or ischemia/reperfusion injury).

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention (e.g., treating, preventing and/or delaying the onset and/or development of heart disease or ischemia/reperfusion injury). The instructions included with the kit generally include information as to the components and their administration to an individual.

The following examples are provided to illustrate various embodiments of the invention, and are not intended to limit the invention in any manner.

EXAMPLES

All HPLC analysis was carried out using a CTC PAL HTS autosampler with a waters 2487 uv detector powered by an Agilent G1312A binary pump. The following method and column were used for determination of retention time (TR) 0-100% B [MeCN:H$_2$O:0.2% HCO$_2$H], 2.5 min gradient, 0.5 min hold, 215 nm, Atlantis dC18 2.1×50 mm, 5 μm.

All NMR were recorded on a Bruker AVANCE 400 MHz, or Bruker 500 spectrometer operating at ambient probe temperature using an internal deuterium lock. Chemical shifts are reported in parts per million (ppm) at lower frequency relative to tetramethylsilane (TMS). Standard abbreviations are used throughout (s singlet; br. s broad singlet; d doublet; dd doublet of doublets; t triplet; q quartet; quin quintet; m multiplet). Coupling constants are reported in Hertz (Hz).

Example 1

Preparation of Compounds of the Invention According to General Synthesis of Scheme A 2-Hydroxysulfamoyl-benzoic acid methyl ester (Compound 1)

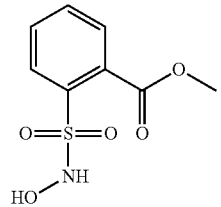

A solution of potassium carbonate (3.53 g, 25.57 mmol) in water (3.6 ml) was added dropwise to a solution of hydroxylamine hydrochloride (1.76 g, 25.57 mmol) in water (2.4 ml) at 0° C. maintaining an internal reaction temperature between 5° C. and 15° C. THF (12 ml) and methanol (3 ml) were added, followed by 2-chlorosulfonyl-benzoic acid methyl ester (3 g, 12.78 mmol) portionwise maintaining a temperature below 15° C. and the reaction mixture was stirred at ambient temperature until complete consumption of the sulfonyl chloride was observed by tlc. The resulting suspension was concentrated to remove any volatiles and the aqueous suspension was extracted with diethyl ether (2×100 ml). The organic portion was dried over sodium sulphate, filtered and concentrated in vacuo to yield the crude N-hydroxy sulfonamide. Purification was achieved by chromatography on silica gel eluting with heptane:ethyl acetate (8:2 v:v) to give the parent compound as a white solid (1.3 g, 44% yield); δH (400

MHz, DMSO) 9.87 (1H, d, 3.4 Hz), 9.39 (1H, d, 3.2 Hz), 7.97 (1H, m), 7.77 (2H, m), 7.68-7.72 (1H, m), 3.83 (3H, s); TR=1.43 min.

Hz), 8.23 (1H, ddd, 7.9, 1.3, 1.2 Hz), 8.06 (1H, ddd, 7.8, 2.0, 1.2 Hz), 7.77 (1H, t, 7.7 Hz); TR=1.19 min.

Example 2

Preparation of Compounds of the Invention According to General Synthesis of Scheme A 3-Hydroxysulfamoyl-benzoic acid (Compound 2)

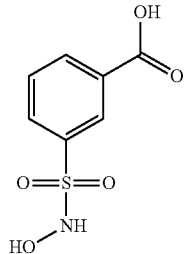

A solution of potassium carbonate (0.43 g, 3.10 mmol) in water (1.2 ml) was added drop wise to a solution of hydroxylamine hydrochloride (0.21 g, 3.10 mmol) in water (0.8 ml) at 0° C. maintaining an internal reaction temperature between 5° C. and 15° C. THF (4 ml) and methanol (1 ml) were added, followed by 3-chlorosulfonyl-benzoic acid (0.34 g, 1.55 mmol) portion wise maintaining a temperature below 15° C. and the reaction mixture was stirred at ambient temperature until complete consumption of the sulfonyl chloride was observed by LCMS. The resulting suspension was concentrated to remove any volatiles and the aqueous suspension was extracted with diethyl ether (2×100 ml), and the combined organic layers were discarded. The aqueous layer was acidified to pH=1, adding a solution of hydrochloric acid (2N) drop wise, then extracted with diethyl ether (2×100 ml). The organic portion was dried over sodium sulphate, filtered and concentrated in vacuo to yield the clean N-hydroxysulphonamide as a yellow solid (0.9 g, 27% yield); δH (400 MHz, DMSO) 13.52 (1H, br. s.), 9.72-9.74 (2H, m), 8.38 (1H, t, 1.6

Example 3

Preparation of Compounds of the Invention According to General Synthesis of Scheme B 4-Bromo-3-(hydroxysulfamoyl)-N,N-dimethylbenzamide (Compound 6)

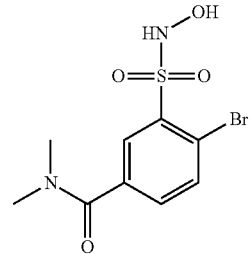 [SMILES: CN(C)C(=O)c1ccc(Br)c(S(=O)(=O)NO)c1]

A solution of aqueous hydroxylamine (0.5 ml of a 50% aqueous solution, 7.6 mmol) in water (1 ml) and THF (5 ml) was cooled to −5° C. 2-Bromo-5-(dimethyl-4-carbonyl)benzene sulfonyl chloride was added portionwise maintaining a temperature below about 10° C. and the reaction mixture was stirred at this temperature until complete consumption of the sulfonyl chloride is observed by thin layer chromatography (TLC). The resulting suspension is concentrated to remove any volatiles and resulting solid was washed with diethyl ether to yield the title compound as a cream solid (0.36 g, 36%). δH (500 MHz, DMSO-d6) 10.00 (1H, br. s), 9.88 (1H, s), 7.95 (1H, d, 1.8 Hz), 7.93 (1H, d, 8.1 Hz), 7.61 (1H, dd, 8.3, 2.0 Hz), 3.00 (3H, s), 2.91 (3H, s), TR=1.19 min.

Using the experimental conditions reported above and detailed in General Synthesis Scheme A and B (Methods 1 and 2) and the appropriate starting materials, which were either commercially available or synthesised using standard literature conditions, the following derivatives were prepared:

| Compound No. | Systematic Name | 1-H NMR | $T_R$ | Method of N-Hydroxy Sulfonamide Synthesis | Yield |
|---|---|---|---|---|---|
| 3 | 4-Chloro-3-hydroxysulfamoyl-benzoic acid | $δ_H$ (400 MHz, DMSO) 13.62 (1H, br. s.), 10.03 (1H, d, 2.9 Hz), 9.88 (1H, d, 2.9 Hz), 8.50 (1H, d, 2.2 Hz), 8.16 (1H, dd, 8.3, 2.2 Hz), 7.82 (1H, d, 8.3 Hz). | 1.24 | A | 25% |
| 4 | 4-Bromo-3-hydroxysulfamoyl-benzoic acid | $δ_H$ (400 MHz, DMSO-d6) 13.63 (1H, s), 10.06 (1H, s), 9.89 (1H, d, 1.7 Hz), 8.50 (1H, d, 1.7 Hz), 7.97-8.06 (3H, m). | 1.28 | A | 33% |
| 5 | -Bromo-N-hydroxy-5-(morpholine-4-carbonyl)-benzenesulfonamide | $δ_H$ (400 MHz, DMSO-d6) 10.02 (1H, br. s.), 9.89 (1H, s), 7.95 (1H, d, 9.3 Hz), 7.96 (1H, d, 3.2 Hz), 7.62 (1H, dd, 8.2, 2.1 Hz), 3.49-3.71 (8H, m). | 1.27 | A | 6% |

| Compound No. | Systematic Name | 1-H NMR | $T_R$ | Method of N-Hydroxy Sulfonamide Synthesis | Yield |
|---|---|---|---|---|---|
| 7 | 4-Chloro-3-(hydroxysulfamoyl)-N,N-dimethylbenzamide | $\delta_H$ (500 MHz, DMSO-d6) 9.97 (1H, s), 9.87 (1H, d, 2.1 Hz), 7.95 (1H, d, 0.8 Hz), 7.69-7.82 (2H, m), 3.00 (3H, br. s), 2.91 (3H, br. s). | 1.18 | B | 79% |
| 8 | N-Hydroxy-2-(morpholin-4-ylsulfonyl)benzene sulfonamide | $\delta_H$ (400 MHz, DMSO-d6) 10.03 (1H, d, 3.4 Hz), 9.18 (1H, d, 3.4 Hz), 8.17-8.23 (1H, m), 8.07-8.14 (1H, m), 7.90-7.97 (2H, m), 3.58-3.64 (4H, m), 3.19-3.25 (4H, m). | 1.05 | B | 26% |
| 9 | -(Morpholin-4-yl)ethyl 4-chloro-3-(hydroxy-sulfamoyl)benzoate | $\delta$H (500 MHz, DMSO-d6) 10.05 (1H, br. s.), 9.89 (1H, s), 8.50 (1H, s), 8.17 (1H, dd, 1.2, 8.4 Hz), 7.87 (1H, d, 8.4 Hz), 4.44 (2H, t, 5.6 Hz), 3.55 (4H, t, 4.4 Hz), 2.70 (2H, t, 5.7 Hz), 2.43-2.49 (4H, m). | 0.86 | B | 23% |
| 97 | 4-Bromo-5-(hydroxysulfamoyl)-N-[2-(morpholin-4-yl)ethyl]thiophene-2-carboxamide | $\delta$H (500 MHz, DMSO-d6) 10.05 (1H, br. s.), 9.95 (1H, s), 8.82 (1H, t, 5.6 Hz), 7.89 (1H, s), 3.56 (4H, t, 4.5 Hz), 3.39-3.37 (2H, m), 2.46 (2H, t, 6.6 Hz), 2.41 (4H, br. s.). | 0.75 | B | 25% |
| 98 | 3-Bromo-N-hydroxy-5-(morpholin-4-ylcarbonyl)thiophene-2-sulfonamide | $\delta$H (500 MHz, DMSO-d6) 10.06 (1H, br. s.), 9.97 (1H, s), 7.61 (1H, s), 3.63-3.60 (8H, m). | 1.24 | B | 43% |

Synthesis of Starting Sulfonyl Chlorides

The sulfonyl chlorides were synthesised from commercially available starting materials following the methods described in *J. Med. Chem*, 40, 2017; *Bioorg. Med. Chem*, 2002, 639-656; *Journal of Pharmacy and Pharmacology*, 1963, 202-211 and in *Australian Journal of Chemistry*, 2000, 1-6. For example, certain sulfonyl chlorides can be synthesized according to the following schemes:

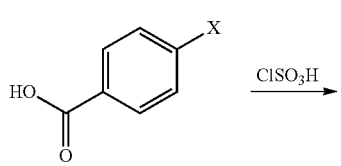

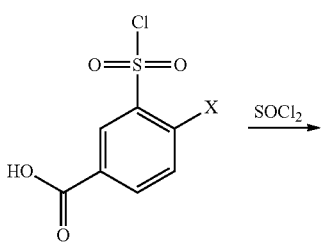

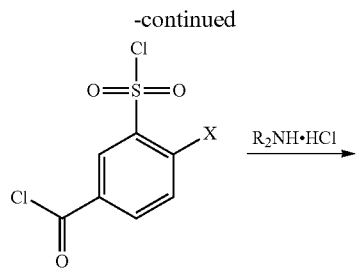

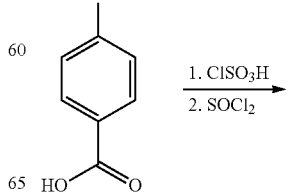

X = Cl, Br

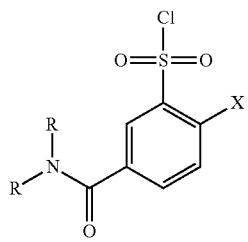

-continued

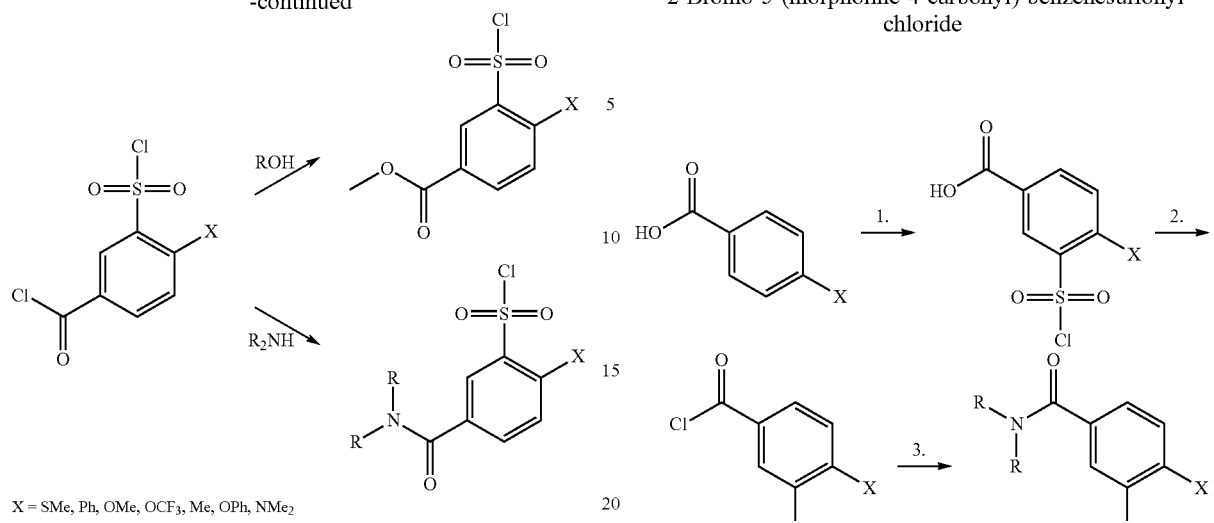

X = SMe, Ph, OMe, OCF₃, Me, OPh, NMe₂

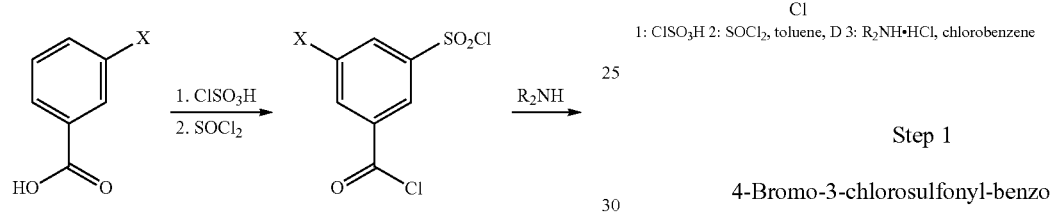

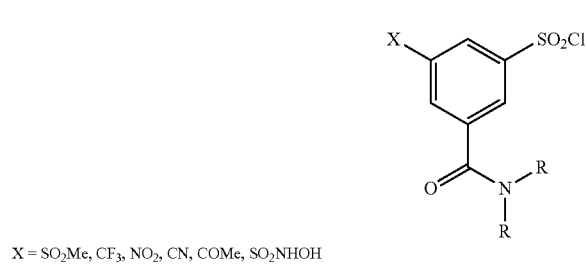

X = SO₂Me, CF₃, NO₂, CN, COMe, SO₂NHOH

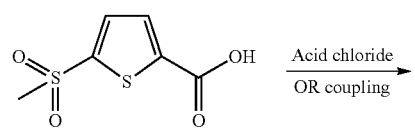

The scheme for thiophene derivatives can be adapted to synthesize similar pyrrole derivatives.

2-Bromo-5-(morpholine-4-carbonyl)-benzenesulfonyl chloride

1: ClSO₃H 2: SOCl₂, toluene, D 3: R₂NH·HCl, chlorobenzene

Step 1

4-Bromo-3-chlorosulfonyl-benzoic acid

4-Bromobenzoic acid (10 g, 49.75 mmol) was added portionwise to chlorosulfonic acid (25 ml, 373.13 mmol) at 0° C. The mixture was heated to 130° C. for 10 hours, until complete consumption of the starting material was observed by LCMS. The reaction mixture was allowed to cool down to ambient temperature, then added drop wise to an ice/water mixture (500 ml). The precipitate was filtered and washed with cold water (2×100 ml). The solid recovered was dissolved in diethyl ether, the solution then dried over sodium sulphate, filtered and concentrated in vacuo to afford the expected product as a beige solid (11.85 g, 79% yield); δH (400 MHz, DMSO) 8.45 (1H, d, 1.7 Hz), 7.72 (1H, d, 2.2 Hz), 7.71 (1H, s); TR=2.08 min.

Step 2

4-Bromo-3-chlorosulfonyl-benzoyl chloride

4-Bromo-3-chlorosulfonyl-benzoic acid (2 g, 6.68 mmol) was suspended in toluene (20 ml). Thionyl chloride (0.97 ml, 13.36 mmol) was added drop wise, and the mixture was heated to reflux for 14 hours under nitrogen until complete consumption of the carboxylic acid was observed by LCMS. The reaction mixture was concentrated under vacuum to dryness to afford the expected acid chloride as a solid (2.12 g, 95% yield). The compound was used for next step without any further purification or analysis; TR=2.38.

Step 3

2-Bromo-5-(morpholine-4-carbonyl)-benzenesulfonyl chloride

Morpholine hydrochloride (0.87 g, 7.01 mmol) was added to a solution of 4-bromo-3-chlorosulfonyl-benzoyl chloride (2.12 g, 6.68 mmol) in chlorobenzene (8 ml). The reaction was heated to reflux for 2 hours, until complete consumption of the starting material was observed by LCMS. The reaction mixture was concentrated to dryness under vacuum. The residue was taken up in diethyl ether (20 ml), and the precipitate was filtered and washed with diethyl ether (2×10 ml), to afford the expected sulfonyl chloride as a beige solid (2.34 g, 95% yield); δH (400 MHz, DMSO) 7.90 (1H, d, 2.2 Hz), 7.64 (1H, d, 8.1 Hz), 7.25 (1H, dd, 8.1, 2.2 Hz), 3.25-3.70 (8H, m); TR=2.01 min.

3-Chlorosulfonyl-4-chloro benzoic acid

3-Chlorosulfonyl-4-chloro benzoic acid was prepared from commercially available starting materials following Step 1 of the above detailed method. δH (400 MHz, DMSO-d6) 14.03 (1H, br. s), 8.43 (1H, d, 2.2 Hz), 7.84 (1H, dd, 8.1, 2.2 Hz), 7.50 (1H, d, 8.1 Hz); TR=1.81 min.

3-Chlorosulfonyl-4-bromo benzoic acid

3-Chlorosulfonyl-4-bromo benzoic acid was prepared from commercially available starting materials following Step 1 of the above detailed method. δH (400 MHz, DMSO) 8.45 (1H, d, 1.7 Hz), 7.72 (1H, d, 2.2 Hz), 7.71 (1H, s); TR=2.08 min.

2-Bromo-5-(dimethyl-4-carbonyl)benzenesulfonyl chloride

2-Bromo-5-(dimethyl-4-carbonyl)benzenesulfonyl chloride was prepared from commercially available starting materials following Steps 1-3 of the above detailed method using dimethylamine HCl instead of morpholine HCl in Step 3. (4.35 g, 80%). δH (500 MHz, DMSO-d6) 7.89 (1H, d, 2.0 Hz), 7.63 (1H, d, 8.1 Hz), 7.25 (1H, dd, 8.1, 2.2 Hz), 2.96 (3H, br. s), 2.88 (3H, br. s); TR=1.78 min.

2-Chloro-5-(dimethyl-4-carbonyl)benzenesulfonyl chloride

2-Chloro-5-(dimethyl-4-carbonyl)benzenesulfonyl chloride was prepared from commercially available starting materials following Steps 1-3 of the above detailed method using dimethylamine HCl instead of morpholine HCl in Step 3. (4.37 g, 79%). δH (500 MHz, DMSO-d6) 7.86 (1H, d, 2.0 Hz), 7.43 (1H, d, 8.1 Hz), 7.34 (1H, dd, 8.1, 2.2 Hz), 2.97 (3H, br. s), 2.90 (3H, br. s); TR=1.20 min.

2-(Morpholin-4-ylsulfonyl)benzene sulfonyl chloride

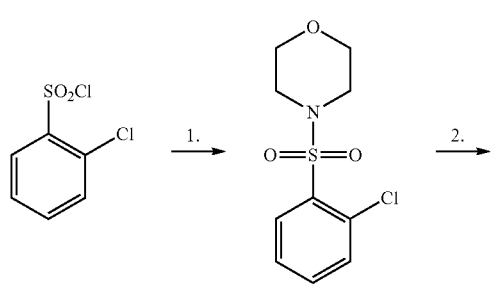

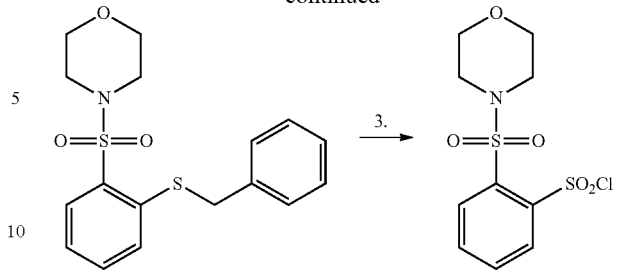

1: morpholine, py, DCM 2: NaSBn, DMSO, 3: Cl2, HCl

Step 1

2-(Morpholin-4-ylsulfonyl)chlorobenzene

To a solution of a 2-chlorobenzene sulfonyl chloride (10 g, 47.4 mmol) in DCM (100 ml) cooled to 0° C. was added pyridine (5.7 ml, 71.1 mmol) and morpholine (6.2 ml, 71.1 mmol) dropwise. Stirring was continued for 15 minutes after which time no sulfonyl chloride was evident by LC-MS. The reaction was quenched by the addition of 2N HCl, washed with further portions of 2N HCl, dried over sodium sulfate, filtered and concentrated in vacuo to yield the title compound without need for additional purification. (11.2 g, 100%). δH (400 MHz, DMSO-d6) 7.97 (1H, dd, 7.8, 1.5 Hz), 7.66-7.77 (2H, m), 7.58 (1H, ddd, 8.1, 6.7, 1.8 Hz), 3.57-3.64 (4H, m), 3.11-3.18 (4H, m); TR=1.25 min.

Step 2

Benzyl-2-(morpholin-4-ylsulfonyl)benzene sulfide

Phenyl methanethiol (7.6 ml, 43.5 mmol) was added dropwise to a 25% solution of NaOMe/MeOH (14.1 g, 65.2 mmol) in MeOH (25 ml). The resulting thiolate was isolated by concentration in vacuo. The sodium thiolate salt was dissolved in DMSO (65 ml), and 2-(morpholin-4-ylsulfonyl) chlorobenzene (11.1 g, 43.5 mmol) added portionwise. The reaction mixture was stirred at ambient temperature for 72 h after which time no starting material was evident. The reaction mixture was poured into a 2N HCl solution (200 mL) and extracted into DCM (3×200 ml). The organic portion was dried over sodium sulfate, filtered and concentrated in vacuo. The crude material was purified by column chromatography eluting with heptane:ethyl acetate (8:2 v:v). (13.7 g, 90%), TR=1.00 min.

Step 3

2-(Morpholin-4-ylsulfonyl)benzene sulfonyl chloride

Chlorine gas was bubbled into a cooled (0° C.) suspension of benzyl-2-(morpholin-4-ylsulfonyl)benzene sulfide (7.0 g, 1.1 mmol) in concentrated HCl (70 ml) maintaining an internal temperature below 15° C. until complete consumption of the starting material was observed (c.a. 45 minutes). After completion of the reaction, nitrogen was bubbled into the reaction mixture for 15 minutes to remove any excess chlorine and the reaction was warmed to ambient temperature. The reaction mixture was poured onto ice and the yellow solid formed was filtered and washed with ice water. The solid was trituated with heptane, filtered and washed with heptane and dried under vacuum to yield the crude sulfonyl chloride as a pale yellow solid which was used directly in the synthesis of Compound 8.

2-(Morpholin-4-yl)ethyl 4-chloro-3-(chlorosulfonyl)benzoate

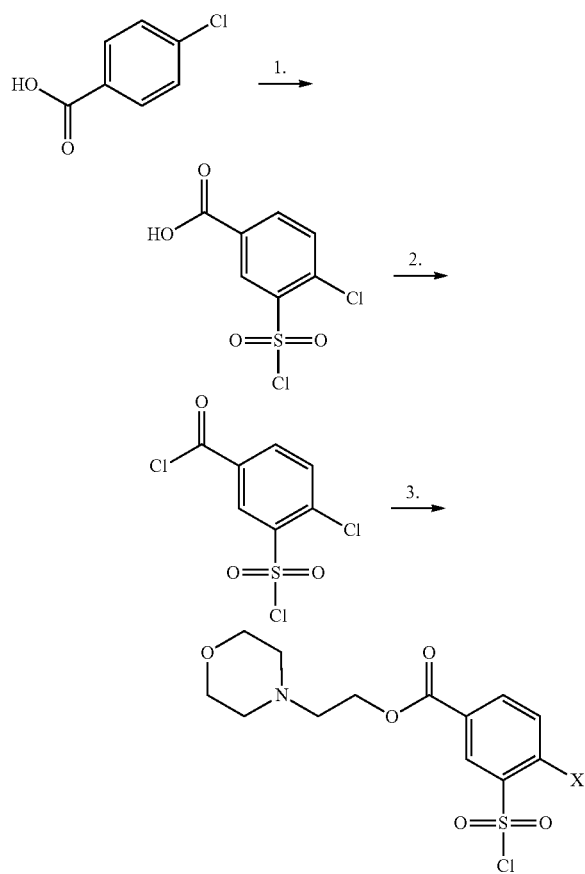

1: ClSO₃H 2: SOCl₂, toluene, Δ 3: hydroxy ethyl morpholine, DCM

The synthesis of 4-chloro-3-(chlorosulfonyl)benzoic acid and 2-chloro-5-(dimethyl-4-carbonyl)benzenesulfonyl chloride were prepared in the same manner as detailed in the synthesis of 2-bromo-5-(morpholine-4-carbonyl)-benzenesulfonyl chloride

Step 3

2-(Morpholin-4-yl)ethyl 4-chloro-3-(chlorosulfonyl)benzoate

To a solution of 4-chloro-3-(chlorosulfonyl)benzoyl chloride (1.0 g, 3.6 mmol) in DCM (10 ml) was added a solution of hydroxy ethyl morpholine (443 μl, 3.6 mmol) in DCM (1 ml). The reaction mixture was stirred for 12 h after which time no sulfonyl chloride was observed by LC-MS. Upon concentration of the crude reaction mixture a solid was isolated, which was triturated with ether to afford the desired compound as a brown solid. (1.54 g, 100%) IR (neat) vmax/cm⁻¹ 1724, 1174, 1450; δH (500 MHz, DMSO-d6) 8.49 (1H, d, 1.8 Hz), 7.97 (1H, dd, 8.2, 1.9 Hz), 7.56 (1H, d, 8.2 Hz), 4.38-5.00 (2H, m), 3.88-4.07 (2H, m), 3.76-3.83 (2H, m), 3.56-3.62 (2H, m), 3.36-3.54 (2H, m), 3.14-3.28 (2H, m).

3-Bromo-5-{[2-(morpholin-4-yl)ethyl] carbamoyl}thiophene-2-sulfonyl chloride 1: RNH₂, DIPEA, DCM 2: ClSO₃H

Step 1

4-Bromo-N-[2-(morpholin-4-yl)ethyl]thiophene-2-carboxamide

To a solution of 4-bromo-2-thiophenecarbonyl chloride (1.0 g, 4.4 mmol) in DCM (10 ml) cooled to 0° C. was added DIPEA (0.85 ml, 4.8 mml) and 4-(2-aminoethyl)morpholine (0.6 ml, 4.6 mmol) dropwise. Stirring was continued until complete consumption of the starting material was observed by LC-MS. The reaction was quenched by the addition of water, which was washed with further portions of 2N HCl, dried over sodium sulfate, filtered and concentrated in vacuo to yield the desired compound without need for further purification (1.6 g, 98%). δH (500 MHz, CHLOROFORM-d) 7.38 (1H, d, 1.3 Hz), 7.37 (1H, d, 1.1 Hz), 3.72-3.80 (4H, m), 3.53 (2H, q, 5.6 Hz), 2.59 (2H, t, 6.0 Hz), 2.48-2.54 (4H, m), TR=0.8 min.

Step 2

3-Bromo-5-{[2-(morpholin-4-yl)ethyl] carbamoyl}thiophene-2-sulfonyl chloride To a flask containing 4-bromo-N-[2-(morpholin-4-yl) ethyl]thiophene-2-carboxamide (1.6 g, 5.1 mmol) was added chlorosulfonic acid (10 ml, 30 equiv). The reaction was heated to 95° C. for 90 minutes before careful addition to ice. The resulting solid was filtered and dried in vacuo. The crude material was triturated with heptane:ethyl acetate to afford the title compound without need for further purification (0.62 g, 29%). δH (500 MHz, DMSO-d6) 9.01 (1H, t, 5.5 Hz), 7.76 (1H, s), 3.97 (2H, d, 10.4 Hz), 3.78 (2H, t, 11.5 Hz), 3.63 (2H, q, 6.0 Hz), 3.51 (2H, d, 12.3 Hz), 3.29 (2H, q, 5.7 Hz), 3.03-3.17 (2H, m), TR=1.22 min.

3-Bromo-5-(morpholin-4-ylcarbonyl)thiophene-2-sulfonyl chloride

Step 1

4-Bromo-N-(morpholin-4-y)thiophene-2-carboxamide

To a solution of 4-bromo-2-thiophenecarbonyl chloride (1.0 g, 4.4 mmol) in DCM (10 ml) cooled to 0° C. was added DIPEA (0.85 ml, 4.8 mmol) and morpholine (0.4 g, 4.6 mmol) dropwise. Stirring was continued until complete consumption of the starting material was observed by LC-MS. The reaction was quenched by the addition of water, which was washed with further portions of 2N HCl, dried over sodium sulfate, filtered and concentrated in vacuo to yield the desired compound without need for further purification (1.2 g, 100%). δH (500 MHz, CHLOROFORM-d) 7.38 (1H, s), 7.18 (1H, s), 3.63-3.83 (8H, m); TR=1.52 min.

Step 2

3-Bromo-5-(morpholin-4-ylcarbonyl)thiophene-2-sulfonyl chloride

To a flask containing 4-bromo-N-(morpholin-4-y)thiophene-2-carboxamide (1.23 g, 4.5 mmol) was added chlorosulfonic acid (9 ml, 30 equiv). The reaction was heated to 95° C. for 90 minutes before careful addition to ice. The resulting suspension was extracted into DCM (3×100 ml) and the combined organic phases dried over sodium sulphate, filtered and concentrated in vacuo to afford the title compound without need for further purification (0.54 g, 32%). δH (500 MHz, CHLOROFORM-d) 7.30 (1H, s) 3.69-3.81 (8H, m), TR=1.86 min.

Example 3

Kinetics of HNO Release

The decomposition rates of the compounds may be determined by UV-Vis spectroscopy.

The decomposition of compounds may be monitored by UV-Vis spectroscopy in 0.1 M PBS buffer at pH 7.4 and 37° C. Bonner, F. T.; Ko., Y. Inorg. Chem. 1992, 31, 2514-2519.

Example 4

HNO Production Via $N_2O$ Quantification

HNO production of the compounds was be determined by UV-Vis spectroscopy.

Nitrous oxide is produced via the dimerization and dehydration of HNO, and is the most common marker for HNO production (Fukuto, J. M.; Bartberger, M. D.; Dutton, A. S.; Paolocci, N.; Wink, D. A.; Houk, K. N. Chem. Res. Toxicol. 2005, 18, 790-801). HNO, however, can also be partially quenched by oxygen to yield a product that does not produce $N_2O$ (See, (a) Mincione, F.; Menabuoni, L.; Briganti, F.; Mincione, G.; Scozzafava, A.; Supuran, C. T. J. Enzyme Inhibition 1998, 13, 267-284 and (b) Scozzafava, A.; Supuran, C. T. J. Med. Chem. 2000, 43, 3677-3687.) Using Angeli's salt (AS) as a benchmark, the relative amounts of $N_2O$ released from compounds are examined via GC headspace analysis.

The ability of compounds to donate nitroxyl at pH 7.4 in PBS buffer at 37° C. was assessed. In particular, the compounds were tested and their nitroxyl donating ability at pH 7.4 in PBS buffer at 37° C. assessed. Results are provided in Table 4 below and results for compounds 1-5 are also illustrated in FIG. 1.

TABLE 4

Nitroxyl Donating Ability of Representative Compounds.

| Compound | Nitrous oxide evolved as % of Angelis salt | % moles $N_2O$/moles of sample |
|---|---|---|
| Angeli's Salt | 100 | 70.5 |
| 1 | 43 | 30.5 |
| 2 | 27 | 19 |
| 3 | 116 | 81.5 |
| 4 | 117 | 82 |
| 5 | 115 | 80.5 |
| 6 | 116 | 81 |
| 7 | 122 | 85 |
| 8 | 126 | 86 |
| 9 | 93 | 65 |
| 97 | 131 | 92 |
| 98 | 116 | 81 |

Example 5

Use of an In Vitro Model to Determine the Ability of Compounds of the Invention to Treat, Prevent and/or Delay the Onset and/or the Development of a Disease or Condition Responsive to Nitroxyl Therapy a. Cardiovascular Diseases or Conditions.

In vitro models of cardiovascular disease can also be used to determine the ability of any of the compounds described herein to treat, prevent and/or delay the onset and/or the development of a cardiovascular disease or condition in an individual. An exemplary in vitro model of heart disease is described below.

In-vitro models could be utilized to look at vasorelaxation properties of the compounds. Isometric tension in isolated rat thoracic aortic ring segment can be measured as described previously by Crawford, J. H., Huang, J, Isbell, T. S., Shiva, S., Chacko, B. K., Schechter, A., Darley-Usmar, V. M., Kerby, J. D., Lang, J. D., Krauss, D., Ho, C., Gladwin, M. T., Patel, R. P., *Blood* 2006, 107, 566-575. Upon sacrifice aortic ring segments are excised and cleansed of fat and adhering tissue. Vessels are then cut into individual ring segments (2-3 mm in width) and suspended from a force-displacement transducer in a tissue bath. Ring segments are bathed at 37° C. in a bicarbonate-buffered, Krebs-Henseleit (K-H) solution of the following composition (mM): NaCl 118; KCl 4.6; $NaHCO_3$ 27.2; $KH_2PO_4$ 1.2; $MgSO_4$ 1.2; $CaCl_2$ 1.75; $Na_2EDTA$, 0.03; and glucose 11.1 and perfused continuously with 21% $O_2$/5% $CO_2$/74% $N_2$. A passive load of 2 g is applied to all ring segments and maintained at this level throughout the experiments. At the beginning of each experiment, indomethacin-treated ring segments are depolarized with KCl (70 mM) to determine the maximal contractile capacity of the vessel. Rings are then washed extensively and allowed to equilibrate. For subsequent experiments, vessels are submaximally contracted (50% of KCl response) with phenylephrine (PE, $3\times10^{-8}$-$10^{-7}$ M), and L-NMMA, 0.1 mM, is also added to inhibit eNOS and endogenous NO production. After tension development reaches a plateau, nitroxyl donating compounds are added cumulatively to the vessel bath and effects on tension monitored.

In vitro models can be utilized to determine the effects of nitroxyl donating compounds in changes in developed force and intracellular calcium in heart muscles. Developed force and intracellular calcium can be measured in rat trabeculae from normal or diseased (i.e. rats with congestive heart failure or hypertrophy) as described previously (Gao W D, Atar D, Backx P H, Marbán E. *Circ Res.* 1995; 76:1036-1048). Rats (Sprague-Dawley, 250-300 g) are used in these experiments. The rats are anesthetized with pentobarbital (100 mg/kg) via intra-abdominal injection, the heart exposed by mid-sternotomy, rapidly excised and placed in a dissection dish. The aorta is cannulated and the heart perfused retrograde (~15 mM/min) with dissecting Krebs-Henseleit (H-K) solution equilibrated with 95% $O_2$ and 5% $CO_2$. The dissecting K-H solution is composed of (mM): NaCl 120, $NaHCO_3$ 20, KCl 5, $MgCl_2$ 1.2, glucose 10, $CaCl_2$ 0.5, and 2,3-butanedione monoximine (BDM) 20, pH 7.35-7.45 at room temperature (21-22° C.). Trabeculae from the right ventricle of the heart are dissected and mounted between a force transducer and a motor arm and superfused with normal K-H solution (KCl, 5 mM) at a rate of ~10 ml/min and stimulated at 0.5 Hz. Dimensions of the muscles are measured with a calibration reticule in the ocular of the dissection microscope (×40, resolution ~10 μm).

Force is measured using a force transducer system and is expressed in milli newtons per square millimeter of cross-sectional area. Sarcomere length is measured by laser diffraction. Resting sarcomere length is set at 2.20-2.30 μm throughout the experiments.

Intracellular calcium is measured using the free acid form of fura-2 as described in previous studies (Gao et al., 1994; Backx et aL, 1995; Gao et al., 1998). Fura-2 potassium salt is microinjected iontophoretically into one cell and allowed to spread throughout the whole muscle (via gap junctions). The tip of the electrode (~0.2 μm in diameter) is filled with fura-2 salt (1 mM) and the remainder of the electrode was filled with 150 mM KCl. After a successful impalement into a superficial cell in non-stimulated muscle, a hyperpolarizing current of 5-10 nA is passed continuously for ~15 min. Fura-2 epifluorescence is measured by exciting at 380 and 340 nm. Fluorescent light is collected at 510 nm by a photomultiplier tube. The output of photomultiplier is collected and digitized. Ryanodine (1.0 μM) is used to enable steady-state activation. After 15 min of exposure to ryanodine, different levels of tetanizations are induced briefly (~4-8 seconds) by stimulating the muscles at 10 Hz at varied extracellular calcium (0.5-20 mM). All experiments are performed at room temperature (20-22° C.).

b. Diseases or Conditions Implicating Ischemia/Reperfusion.

In vitro models can also be used to determine the ability of any of the compounds described herein to treat, prevent and/or delay the onset and/or the development of a disease or condition implicating ischemia/reperfusion injury in an individual.

Example 6

Use of In Vivo and/or Ex Vivo Models to Determine the Ability of Compounds of the Invention to Treat, Prevent and/or Delay the Onset and/or the Development of a Disease or Condition Responsive to Nitroxyl Therapy a. Cardiovascular Diseases or Conditions.

In vivo models of cardiovascular disease can also be used to determine the ability of any of the compounds described herein to treat, prevent and/or delay the onset and/or the development of a cardiovascular disease or condition in an individual. An exemplary animal model of heart disease is described below.

In vivo cardiovascular effects obtained with a nitroxyl donor compound may be assessed in a control (normal) dog. The study is conducted in adult (25 kg) mongrel (male) dogs chronically instrumented for conscious hemodynamic analysis and blood sampling, as previously described (Katori, T.; Hoover, D. B.; Ardell, J. L.; Helm, R. H.; Belardi, D. F.; Tocchetti, C. G.; Forfia, P. R.; Kass, D. A.; Paolocci, N. *Circ. Res.* 96(2): 2004). Micromanometer transducers in the left ventricle provide pressure, while right atrial and descending aortic catheters provide fluid-pressures and sampling conduits. Endocardial sonomicrometers (anteriorposterior, septal-lateral) measure short-axis dimensions, a pneumatic occluder around the inferior vena cave facilitated pre-load manipulations for pressure-relation analysis. Epicardial pacing leads are placed on the right atrium, and another pair is placed on the right ventricle free wall linked to a permanent pacemaker to induce rapid pacing-cardiac failure. After 10 days of recovery, animals are evaluated at baseline sinus rhythm and with atrial pacing (120-160 bpm). Measurements include conscious hemodynamic recordings for cardiac mechanics.

Compounds of the invention are administrated to a healthy control dog at the dose of 1-5 μg/kg/min and the resulting cardiovascular data is obtained.

Demonstration that a compound of the invention improves cardiac hemodynamics in hearts with congestive failure: After completing protocols under baseline conditions, congestive heart failure is induced by tachypacing (210 bpm×3 weeks, 240 bpm×I week), as previously described (Katori, T.; Hoover, D. B.; Ardell, J. L.; Helm, R. H.; Belardi, −37 D. F.; Tocchetti, C. G.; Forfia, P. R.; Kass, D. A.; Paolocci, N. *Circ. Res.* 96(2): 2004). Briefly, end-diastolic pressure and +dP/dt, max are measured weekly to monitor failure progression. When animals demonstrate a rise in EDP more than 2×, and dp/dt,max of >50% baseline, they are deemed ready for congestive heart failure studies.

The values for test compounds are obtained after 15 min continuous i.v. infusion (2.5 or 1.25 μg/kg/min) in control and heart failure preparations, respectively, both in the absence and in the presence of volume restoration. For comparison, the same hemodynamic measurements are obtained with AS in heart failure preparations.

b. Diseases or Conditions Implicating Ischemia/Reperfusion.

Ex-vivo models of ischemia/reperfusion can also be used to determine the ability of any of the compounds described herein to treat, prevent and/or delay the onset and/or the development of a disease or condition implicating ischemia/reperfusion injury in an individual. An exemplary ex vivo model of ischemia/reperfusion injury is described below.

Male Wistar rats are housed in identical cages and allowed access to tap water and a standard rodent diet ad libitum. Each animal is anesthetized with 1 g/kg urethane i.p. 10 min after heparin (2,500 U, i.m.) treatment. The chest is opened, and the heart is rapidly excised, placed in ice-cold buffer solution and weighed. Isolated rat hearts are attached to a perfusion apparatus and retrogradely perfused with oxygenated buffer solution at 37° C. The hearts are instrumented as previously described in Rastaldo et al., "P-450 metabolite of arachidonic acid mediates bradykinin-induced negative inotropic effect," *Am. J. Physiol.*, 280:H2823-H2832 (2001), and Paolocci et al. "cGMP-independent inotropic effects of nitric oxide and peroxynitrite donors: potential role for nitrosylation," *Am. J. Physiol.*, 279: H1982-H1988 (2000). The flow is maintained constant (approximately 9 mL/min/g wet weight) to reach a typical coronary perfusion pressure of 85-90 mm Hg. A constant proportion of 10% of the flow rate is applied by means of one of two perfusion pumps (Terumo, Tokyo, Japan) using a 50 mL syringe connected to the aortic cannula. Drug applications are performed by switching from the syringe containing buffer alone to the syringe of the other pump containing the drug (nitroxyl donating compound) dissolved in a vehicle at a concentration 10× to the desired final concentration in the heart. A small hole in the left ventricular wall allows drainage of the thebesian flow, and a polyvinyl-chloride balloon is placed into the left ventricle and connected to an electromanometer for recording of left ventricular pressure (LVP). The hearts are electrically paced at 280-300 bpm and kept in a temperature-controlled chamber (37° C.). Coronary perfusion pressure (CPP) and coronary flow are monitored with a second electromanometer and an electromagnetic flow-probe, respectively, both placed along the perfusion line. Left ventricular pressure, coronary flow and coronary perfusion pressure are recorded using a TEAC R-71 recorder, digitized at 1000 Hz and analyzed off-line with DataQ-Instruments/CODAS software, which allow quantification of the maximum rate of increase of LVP during systole ($dP/dt_{max}$).

Hearts are perfused with Krebs-Henseleit solution gassed with 95% $O_2$ and 5% $CO_2$ of the following composition: 17.7 mM sodium bicarbonate, 127 mM NaCl, 5.1 mM KCl, 1.5 mM $CaCl_2$, 1.26 mM $MgCl_2$, 11 mM D-glucose, supplemented with 5 µg/mL lidocaine.

Experimental Compounds. The nitroxyl donors are diluted in buffer immediately prior to use.

Experimental Protocols. Hearts are allowed to stabilize for 30 min, and baseline parameters are recorded. Typically, coronary flow is adjusted within the first 10 min and kept constant from thereon. After 30 min stabilization, hearts are randomly assigned to one of the treatment groups, and subjected to 30 min global, no-flow ischemia, followed by 30 min of reperfusion (I/R). Pacing of the hearts is stopped at the beginning of the ischemic period and restarted after the third minute of reperfusion.

Hearts in a control group are perfused with buffer for an additional 29 min after stabilization. Treated hearts are exposed to a nitroxyl donor (e.g., 1 µM final concentration for about 20 min followed by a 10 min buffer wash-out period).

In all hearts pacing is suspended at the onset of ischemia and restarted 3 minutes following reperfusion. As isolated heart preparations may deteriorate over time (typically after 2-2.5 hrs perfusion), the re-flow duration is limited to 30 min in order to minimize the effects produced by crystalloid perfusion on heart performance, and consistently with other reports.

Assessment of ventricular function. To obtain the maximal developed LVP, the volume of the intra-ventricular balloon is adjusted to an end-diastolic LVP of 10 mm Hg during the stabilization period, as reported in Paolocci, supra, and Hare et al., "Pertussis toxin-sensitive G proteins influence nitric oxide synthase III activity and protein levels in rat hearts," *J. Clin. Invest.*, 101:1424-31 (1998). Changes in developed LVP, $dP/dt_{max}$ and the end-diastolic value induced by the I/R protocol are continuously monitored. The difference between the end-diastolic LVP (EDLVP) before the end of the ischemic period and during pre-ischemic conditions is used as an index of the extent of contracture development. Maximal recovery of developed LVP and $dP/dt_{max}$ during reperfusion is compared with respective pre-ischemic values.

Assessment of myocardial injury. Enzyme release is a measure of severe myocardial injury that has yet to progress to irreversible cell injury. Samples of coronary effluent (2 mL) are withdrawn with a catheter inserted into the right ventricle via the pulmonary artery. Samples are taken immediately before ischemia and at 3, 6, 10, 20 and 30 min of reperfusion. LDH release is measured as previously described by Bergmeyer & Bernt, "Methods of Enzymatic Analysis," *Verlag Chemie* (1974). Data are expressed as cumulative values for the entire reflow period.

To corroborate the data relative to myocardial injury, determined by LDH release, infarct areas are also assessed in a blinded fashion. At the end of the course (30 min reperfusion), each heart is rapidly removed from the perfusion apparatus, and the LV dissected into 2-3 mm circumferential slices. Following 15 min of incubation at 37° C. in 0.1% solution of nitro blue tetrazolium in phosphate buffer as described in Ma et al., "Opposite effects of nitric oxide and nitroxyl on postischemic myocardial injury," *Proc. Natl. Acad. Sci.*, 96:14617-14622 (1999), unstained necrotic tissue is separated from the stained viable tissue. The areas of viable and necrotic tissue are carefully separate by and independent observer who is not aware of the origin of the hearts. The weight of the necrotic and non-necrotic tissues is then determined and the necrotic mass expressed as a percentage of total left ventricular mass.

Data may be subjected to statistical methods such as ANOVA followed by the Bonferroni correction for post hoc t tests.

Example 7

Use of Human Clinical Trials to Determine the Ability to Combination Therapies of the Invention to Treat, Prevent and/or Delay the Onset and/or the Development of a Disease or Condition Responsive to Nitroxyl Therapy If desired, any of the compounds described herein can also be tested in humans to determine the ability of the compound to treat, prevent and/or delay the onset and/or the development of a disease or condition responsive to nitroxyl therapy. Standard methods can be used for these clinical trials. In one exemplary method, subjects with such a disease or condition, such as congestive heart failure, are enrolled in a tolerability, pharmacokinetics and pharmacodynamics phase I study of a therapy using the compounds of the invention in standard protocols. Then a phase II, double-blind randomized controlled trial is performed to determine the efficacy of the compounds using standard protocols.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references, publications, patents, and patent applications disclosed herein are hereby incorporated by reference in their entireties.

The invention claimed is:
1. A compound of the formula (III):

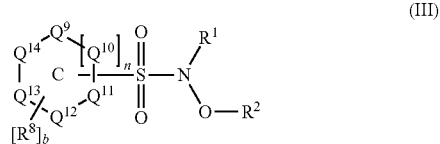

or a pharmaceutically acceptable salt thereof, wherein:
$R^1$ is H;
$R^2$ is H, aralkyl or heterocyclyl;
n is the integer 0 or 1;
b is an integer from 1-4;
each $R^8$ is independently selected from halo, alkylsulfonyl, N-hydroxylsulfonamidyl, perhaloalkyl, nitro, aryl, cyano, alkoxy, perhaloalkoxy, alkyl, substituted aryloxy, alkylsulfanyl, alkylsulfinyl, heterocycloalkyl, substituted heterocycloalkyl, dialkylamino, $NH_2$, OH, C(O)OH, C(O)Oalkyl, NHC(O)alkylC(O)OH, C(O)$NH_2$, NHC(O)alkylC(O)alkyl, NHC(O)alkenylC(O)OH, NHC(O)$NH_2$, OalkylC(O)Oalkyl, NHC(O)alkyl, C(=N—OH)NH$_2$, cycloalkoxy, cycloalkylsulfanyl, arylsulfanyl, arylsulfinyl, carbonylamino and sulfonylamino, provided that at least one R$^8$ is carbonylamino or sulfonylamino;

C is a heteroaromatic ring containing ring moieties Q$^9$, Q$^{10}$, Q$^{11}$, Q$^{12}$, Q$^{13}$ and Q$^{14}$ that are independently selected from the group consisting of C, CH, N, NR$^{10}$, O and S, provided that at least one of Q$^9$, Q$^{10}$, Q$^{11}$, Q$^{12}$, Q$^{13}$ and Q$^{14}$ is N, NR$^{10}$, O or S, and R$^{10}$ is H, alkyl, acyl or sulfonyl.

2. The compound of claim 1 or a pharmaceutically acceptable salt thereof, wherein R$^2$ is H.

3. The compound of claim 1 or a pharmaceutically acceptable salt thereof, wherein each R$^8$ is independently selected from Cl, F, I, Br, SO$_2$CH$_3$, SO$_2$NHOH, CF$_3$, CH$_3$, NO$_2$, phenyl, CN, OCH$_3$, OCF$_3$, t-Bu, O-iPr, 4-nitrophenyloxy, —SCH(CH$_3$)$_2$, —S(O)CH(CH$_3$)$_2$, morpholino, N-methylpiperazino, dimethylamino, piperidino, cyclohexyloxy, cyclopentylsulfanyl, phenylsulfanyl, phenylsulfinyl, carbonylamino and sulfonylamino.

4. The compound of claim 1 or a pharmaceutically acceptable salt thereof, wherein each R$^8$ is independently selected from F, Br, Cl, CF$_3$, phenyl, methyl, SO$_2$NHOH, morpholino, piperidino, 4-methyl-piperazino, carbonylamino and sulfonylamino.

5. The compound of claim 1 or a pharmaceutically acceptable salt thereof, wherein:
R$^2$ is H, benzyl or tetrahydropyran-2-yl.

6. The compound of claim 5 or a pharmaceutically acceptable salt thereof, wherein:
n is 0; and
C is a thiophene, isoxazole, pyrazole, pyrrole, imidazole, furan, thiazole, triazole, N-methylimidazole or thiadiazole.

7. The compound of claim 5 or a pharmaceutically acceptable salt thereof, wherein:
C is thiophene; and
b is 1.

8. The compound of claim 2 or a pharmaceutically acceptable salt thereof, wherein:
C is thiophene; and
at least one R$^8$ is a carbonylamino having the formula —CONR$_2$ wherein each R is taken together with the nitrogen to which it is attached to form a heterocyclic ring or a substituted heterocyclic ring.

9. A compound which is:

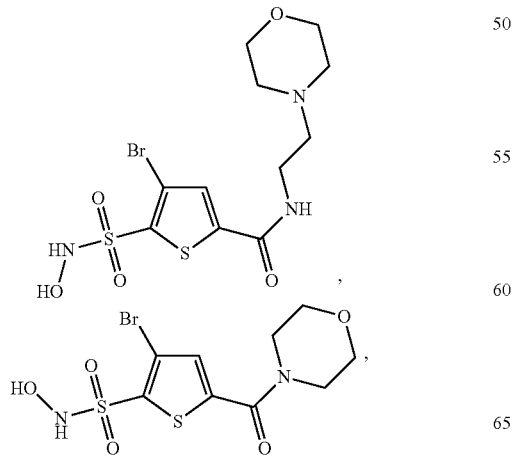

-continued

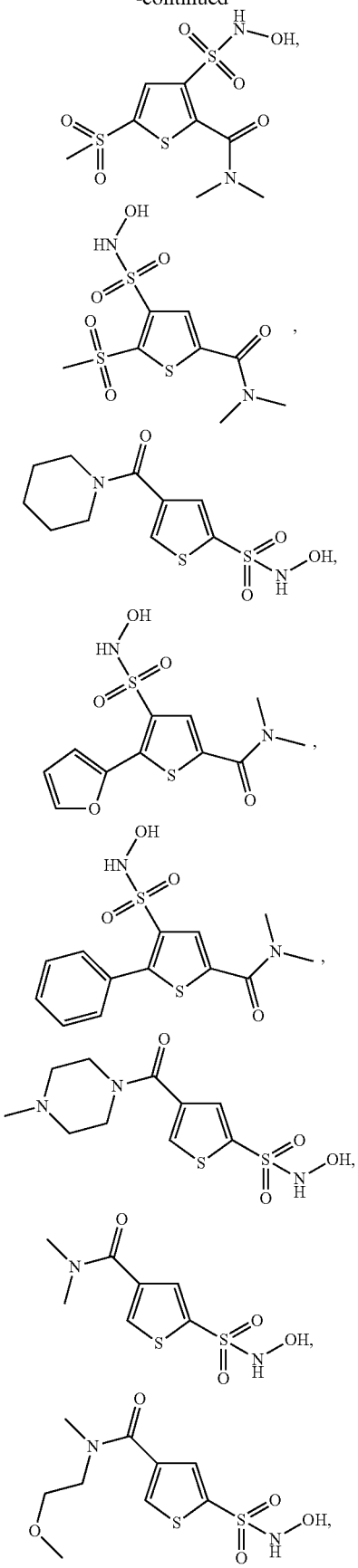

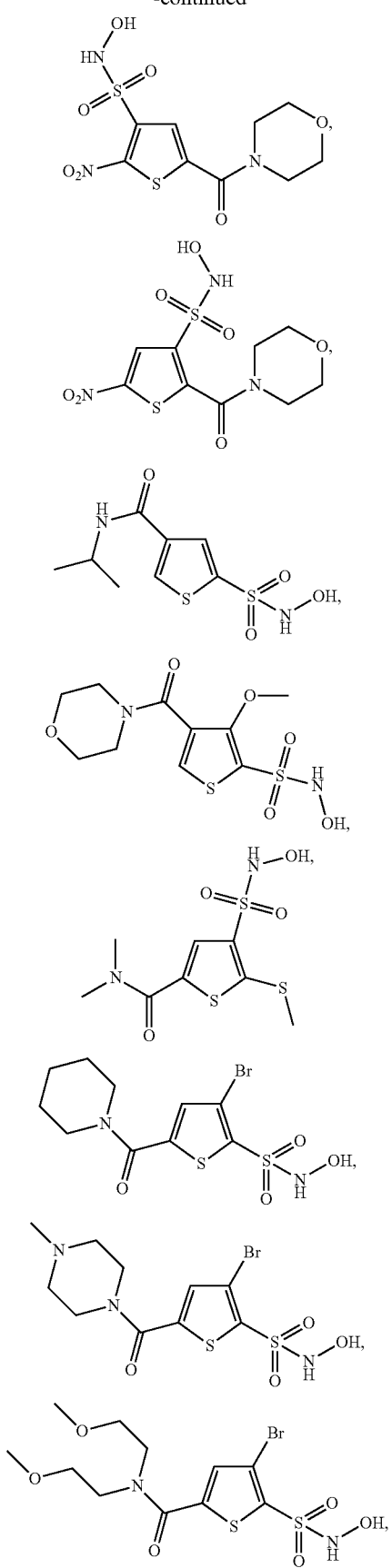

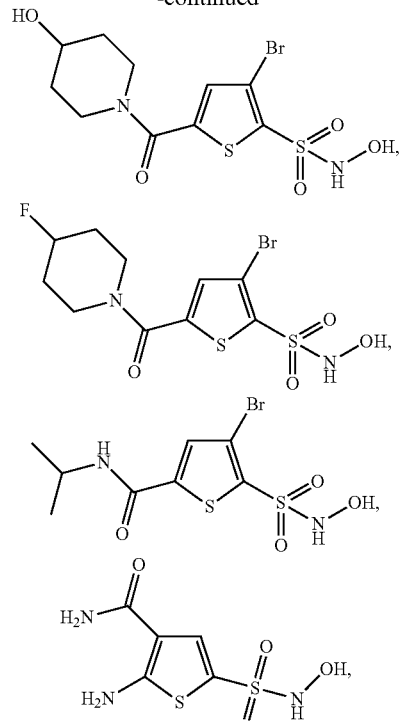

or a pharmaceutically acceptable salt thereof.

10. A pharmaceutical composition comprising a compound of claim 1 or a pharmaceutically acceptable salt thereof and a pharmaceutically acceptable carrier.

11. A kit comprising a compound of the claim 1 or a pharmaceutically acceptable salt thereof and instructions for use in the treatment of a disease or condition that is responsive to nitroxyl therapy.

12. A pharmaceutical composition comprising a compound of claim 9 or a pharmaceutically acceptable salt thereof and a pharmaceutically acceptable carrier.

13. The compound of claim 1 or a pharmaceutically acceptable salt thereof, wherein:
C is thiophene;
$R^2$ is H; and
at least one $R^8$ is a carbonylamino having the formula —$CONR_2$ wherein each R is taken together with the nitrogen to which it is attached to form morpholino or substituted morpholino.

14. The compound of claim 13 or a pharmaceutically acceptable salt thereof, wherein the morpholino formed from each R taken together with the $R^8$—$CONR_2$ carbonylamino group nitrogen to which it is attached is unsubstituted.

15. The compound of claim 1 or a pharmaceutically acceptable salt thereof, wherein:
C is thiophene;
$R^2$ is H; and
b is 1 or 2; and
at least one $R^8$ is a carbonylamino having the formula —$CONR_2$ wherein each R is taken together with the nitrogen to which it is attached to form a heterocyclic ring selected from piperidinyl and morpholinyl and, when b is 2, an $R^8$ that is other than —$CONR_2$ is selected from halo, nitro and —O-alkyl.

16. The compound of claim 15 or a pharmaceutically acceptable salt thereof, wherein b is 1.

17. The compound of claim 7 or a pharmaceutically acceptable salt thereof, wherein $R^8$ is a carbonylamino having the formula —CONH-alkyl.

18. The compound of claim 17 or a pharmaceutically acceptable salt thereof, wherein $R^2$ is H.

19. The compound of claim 18 or a pharmaceutically acceptable salt thereof, wherein the alkyl of the $R^8$—CONH-alkyl carbonylamino group is isopropyl.

20. The compound of claim 7 or a pharmaceutically acceptable salt thereof, wherein $R^8$ is a carbonylamino having the formula —CONR-alkyl wherein R is alkyl.

21. The compound of claim 20 or a pharmaceutically acceptable salt thereof, wherein $R^2$ is H.

22. The compound of claim 21 or a pharmaceutically acceptable salt thereof, wherein each alkyl of the $R^8$—CONR-alkyl carbonylamino group is selected from methyl, ethyl, n-propyl, i-propyl, t-butyl, n-heptyl, and octyl.

* * * * *